(12) United States Patent
Park et al.

(10) Patent No.: US 7,244,805 B2
(45) Date of Patent: Jul. 17, 2007

(54) BIMETALLIC ZINC COMPLEX AND PROCESS OF PRODUCING POLYCARBONATE USING THE SAME AS POLYMERIZATION CATALYST

(75) Inventors: Young Whan Park, Daejeon (KR); Hyo Sun Lee, Daejeon (KR); Young Chul Won, Suwon (KR); Bun Yeoul Lee, Suwon (KR); Heon Yong Kwon, Kyungsangnam-do (KR); Soo Yeon Lee, Wonju (KR)

(73) Assignee: LG Chem Ltd., Seoul (KR)

( * ) Notice: Subject to any disclaimer, the term of this patent is extended or adjusted under 35 U.S.C. 154(b) by 113 days.

(21) Appl. No.: 11/088,806

(22) Filed: Mar. 25, 2005

(65) Prior Publication Data

US 2006/0135743 A1 Jun. 22, 2006

(30) Foreign Application Priority Data

Dec. 16, 2004 (KR) ...................... 10-2004-0107214

(51) Int. Cl.
*C08G 64/00* (2006.01)
(52) U.S. Cl. ..................... 528/198; 424/63; 424/94; 435/6; 514/6; 524/104; 568/583; 568/587
(58) Field of Classification Search ............. 424/94.63; 435/6; 514/6; 524/104; 568/583, 587
See application file for complete search history.

(56) References Cited

U.S. PATENT DOCUMENTS 6,133,402 A 10/2000 Coates et al.
6,610,889 B2 * 8/2003 Trost et al. ................. 568/313

OTHER PUBLICATIONS

Angew. Chem. Int. Ed. 2002, 41, No. 14 (2002) "*Electronic and Steric Effects on Catalysts for CO₂/ Epoxide Polymerization: Subtle Modifications Resulting in Superior Activites*"; David Moore, et al.
The Royal Society of Chemistry(2001) "*Polymer Supported Chromium Porphyrin As Catalyst for Polycarbonate Formation in Supercritical Carbon Dioxide*" Louise M. Stamp, et al.
American Chemical Society(1983) "*Activation of Carbon Dioxide with Aluminum Porphyrin and Reaction with Epoxide. Studies on (Tetraphenylporphinato) Aluminum Alkoxide Having a Long Oxyalkylene Chain as the Alkoxide Group*" Takuzo Aida, et al.
American Chemical Society (1998) "*Catalytic Reactions Involving $C_1$ Feedstocks: New High-Activity Zn(II)-Based Catalysts for the Alternating Copolymerization of Carbon Dioxide and Epoxides*" Ming Cheng, et al.
American Chemical Society (2001) "*Single-Site B-Diiminate Zinc Catalysts for the Alternating Copolymerization of $CO_2$ and Epoxides: Catalyst Synthesis and Unprecedented Polymerization Activity*" Ming Cheng, et al.
J. AM. Chem. Soc. (2002) "*Mechanistic Aspects of the Copolymerization Reaction of Carbon Dioxide and Epoxides, Using a Chiral Salen Chromium Chloride Catalyst*" Donald J. Darensbourg, et al.
J. AM. Chem. Soc. (2003) "*Mechanism of the Alternating Copolymerization of Epoxides and $CO_2$ Using B-Diiminate Zinc Catalysts: Evidence for a Bimetallic Epoxide Enchainment*" David R. Moore, et al.
American Chemical Society(1995) "*Catalytic Formation of Cyclic Carbonates from Epoxides and $CO_2$ with Chromium Metalloporphyrinates*" William J. Kruper, et al.
American Chemical Society(1995) "*Catalytic Activity of Zinc (II) Phenoxides Which Possess Readily Accessible Coordination Sites. Copolymerization and Terpolymerization of Epoxides and Carbon Dioxide*" Donald Darensbourg, et al.
American Chemical Society (1997)"*Copolymerization of 1, 2-Epoxycyclohexane and Carbon Dioxide Using Carbon Dioxide as Both Reactant and Solvent*" Michael Super, et al.
American Chemical Society(2000) "*Copolymerization of $CO_2$ and 1,2-Cyclohexene Oxide Using a $CO_2$- Soluble Chromium Porphyrin Catalyst*" Stephen Mang, et al.
The British Library (1969) "*Copolymerization of Carbon Dioxide and Epoxide*".

* cited by examiner

*Primary Examiner*—Terressa Boykin
(74) *Attorney, Agent, or Firm*—McKenna Long & Aldridge LLP

(57) ABSTRACT

Provided are a bimetallic zinc complex and a method of producing polycarbonate, including polymerizing an epoxy compound and carbon dioxide using the bimetallic zinc complex. The bimetallic zinc complex according to the present invention has a distance between zinc-zinc atoms, which is maintained in a limited range regardless of its concentration in a reaction medium for the polymerization. Thus, the bimetallic zinc complex can have a polymerization activity even at a high ratio of monomer/catalyst, thereby reducing a catalyst amount to be used, which is economically advantageous. Further, the bimetallic zinc complex can produce a high molecular weight polycarbonate.

7 Claims, 2 Drawing Sheets

BIMETALLIC ZINC COMPLEX AND PROCESS OF PRODUCING POLYCARBONATE USING THE SAME AS POLYMERIZATION CATALYST

BACKGROUND OF THE INVENTION

This application claims the benefit of Korean Patent Application No. 10-2004-0107214, filed on Dec. 16, 2004, in the Korean Intellectual Property Office, the disclosure of which is incorporated herein in its entirety by reference.

1. Field of the Invention

The present invention relates to a catayst used in producing polycarbonate from an epoxy compound and carbon dioxide and a method of producing polycarbonate using the catalyst, and more particularly, to a bimetallic coordinating compound in which ligands coordinated to two metal atoms are linked via a spacer, the bimetallic coordinating compound being used in producing polycarbonate, and a method of producing polycarbonate using the compound.

2. Description of the Related Art

Polycarbonates are easily biodegradable and useful as, for example, packages or coating materials. Since 1960s, many researchers have developed various types of catalysts used in producing polycarbonate from an epoxy compound and carbon dioxide and most of the developed catalysts are metallic zinc compounds.

The methods of producing polycarbonate from an epoxy compound and carbon dioxide are very environment-friendly since phosgene, a toxic compound, is not required and carbon dioxide can be obtained from the air.

Inoue, S. et al. reported a method of producing polycarbonate using a non-uniform catalyst obtained by partially hydrolyzing a zinc diethyl compound (J. Poly. Sci. Lett. B7, 287-292 (1969)). However, the catalyst has a very low activity.

Aida, T. et al. reported a method of producing polycarbonate using an aluminum porpyrin catalyst (J. Am. Chem. Soc. 105, 1304-1309 (1983)). This catalyst has a turnover rate of 0.3 turnover/hr or less, i.e., has a low activity.

D. J. Darensbourg described an improved method of producing polycarbonate using a well-defined zinc complex and obtained a turnover rate of 2.4 turnover/h (Macromolecules, 28, 7577-7579 (1995)). M. Super et al., described other improved method of producing polycarbonate using a catalyst compound obtained from zinc oxide, of which chemical structure is not clearly defined, and obtained a turnover rate of 8.4 turnover/hr (Macromolecules, 30, 368-372 (1997)). However, since the activities of these catalysts are low, the catalysts cannot be used. When these catalysts are used, phenoxy composing ligands of the catalysts are introduced into ends of the polymer chains.

Coates, G. W. et al. developed a highly active catalyst by using a zinc complex comprising β-diketiminate ligand (U.S. Pat. No. 6,133,402). According to the substituent of the β-diketiminate ligand, a maximum turnover rate of 1,116 turnover/hr can be obtained. The research group of Coates, G. W. obtained a maximum turnover rate of 2,300 turnover/hr using a zinc catalyst having a similar structure (J. Am. Chem. Soc. 125, 11911-11924 (2003)).

In addition, methods using chromium-based catalysts were reported (Kruper, W. J. et al., J. Org. Chem. 60, 725-727 (1995), Mang, S. et al., Macromolecules, 33, 303-308 (2000), Stamp, L. M. et al., Chem. Commun. 2001, 2502-2503, Darensbourg, D. J. et al., J. Am. Chem. Soc. 124, 6335-6342 (2002)). In these methods, catalytic activities are lower than the zinc catalysts.

According to the research results of the research group of Coates, G. W. (J. Am. Chem. Soc. 125, 11911-11924 (2003)), for the zinc complexes comprising β-diketiminate ligand to catalyze the production of polycarbonate from an epoxy compound and carbon dioxide, a cooperative operation of two zinc complexes is required. To ensure that the cooperative operation occurs according to the reaction mechanism, a distance between zinc-zinc atoms should be maintained appropriate for the polymerization reaction.

That is, when bulkiness of the substituent of β-diketiminate ligand is too low and the distance between zinc-zinc atoms is too short, an interaction between two zinc coordinate compounds is too strong. Thus, the polymerization does not proceed. Contrary to this, when bulkiness of the substituent of β-diketiminate ligand is too high and the distance between zinc-zinc atoms is too long, a monomer coordinated to one zinc atom cannot be easily transferred to a polymer chain coordinated to the other zinc atom, and thus a rate of the polymerization reaction is low. Thus, in this method, the catalytic activity was maximized by controlling the bulkiness of the substituent to maintain the appropriate distance between zinc-zinc atoms. However, since a probability that the cooperative operation of the two zinc complexes occurs during the polymerization reaction is too low when the concentration of the catalyst in a polymerization reaction system is too low, a very low ratio of monomer/catalyst must be maintained. For this reason, they suggested in U.S. Pat. No. 6,133,402 that a ratio of monomer/catalyst be limited to 100-4,000. Accordingly, the method is not suitable for producing a polymer having a high molecular weight. In the method, a maximum turnover per catalyst molecule is about 1,116 and a number average molecular weight of the resultant polymer is 5,000-40,000.

SUMMARY OF THE INVENTION

The present invention provides a bimetallic zinc complex which has a polymerization activity even at a high ratio of monomer/catalyst, thereby reducing a catalyst amount to be used, which is economically advantageous.

The present invention also provides a method of producing a high molecular weight polycarbonate using the bimetallic zinc complex as a catalyst.

The present invention also provides a high molecular weight polycarbonate produced using the method.

According to an aspect of the present invention, there is provided a bimetallic zinc complex having formula 1:

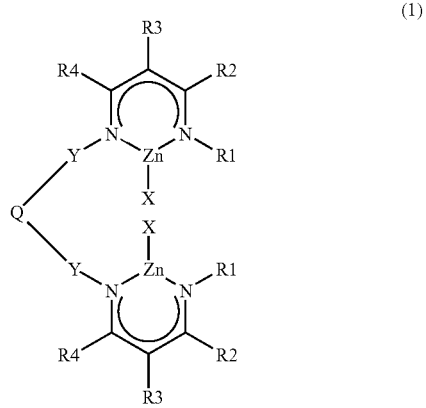

(1)

wherein each of N~N chelate ligands is a monovalent anion and together with zinc forms a 6-membered ring, R1 is a $C_1$-$C_{20}$ alkyl radical having at least one hydrogen atom unsubstituted or substituted by a halogen atom or a $C_6$-$C_{20}$ aryl radical having at least one hydrogen atom unsubstituted or substituted by a halogen atom, and the R1 radicals are either identical or different from each other, R2 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R2 radicals are either identical or different from each other, R3 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R3 radicals are either identical or different from each other, R4 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R4 radicals are either identical or different from each other, either R2 and R3, or R3 and R4 may be linked to each other to form a ring, X is a monovalent anion selected from a $C_1$-$C_{20}$ alkoxy radical having at least one hydrogen atom unsubstituted or substituted by a halogen atom, carboxy, alkylsulfinato, and amido, and the X monovalent anions are either identical or different from each other and each X may be coordinated to only a metallic zinc atom or form a bridged structure between two metallic zinc atoms, Y is a carbon diradical and may have at least one hydrogen substituted by halogen, and the Y diradicals are either identical or different from each other, and Q is a $C_1$-$C_{20}$ alkyl diradical having at least one hydrogen atom unsubstituted or substituted by a halogen atom or a $C_6$-$C_{20}$ aryl diradical having at least one hydrogen atom unsubstituted or substituted by a halogen atom.

According to another aspect of the present invention, there is provided a method of producing polycarbonate, comprising:

polymerizing an epoxy compound and carbon dioxide using the above bimetallic zinc complex as a catalyst, the epoxy compound being selected from the group consisting of $C_2$-$C_{20}$ alkylene oxide unsubstituted or substituted by a halogen atom or alkoxy, $C_4$-$C_{20}$ cycloalkene oxide unsubstituted or substituted by a halogen atom or alkoxy, or $C_4$-$C_{10}$ styrene oxide unsubstituted or substituted by a halogen atom, alkoxy, or alkyl.

According to a still another aspect of the present invention, there is provided a polycarbonate produced using the above method.

According to a yet another aspect of the present invention, there is provided a compound having formula 3:

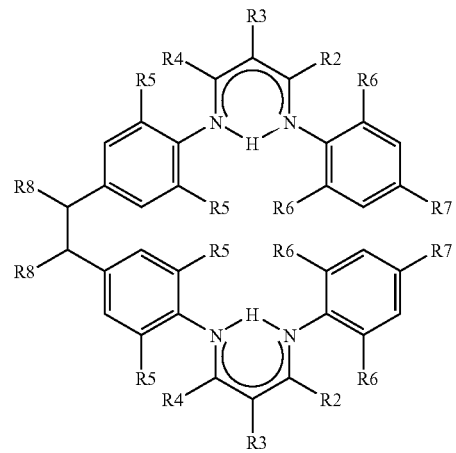

wherein
R2 through R8 are as described above.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
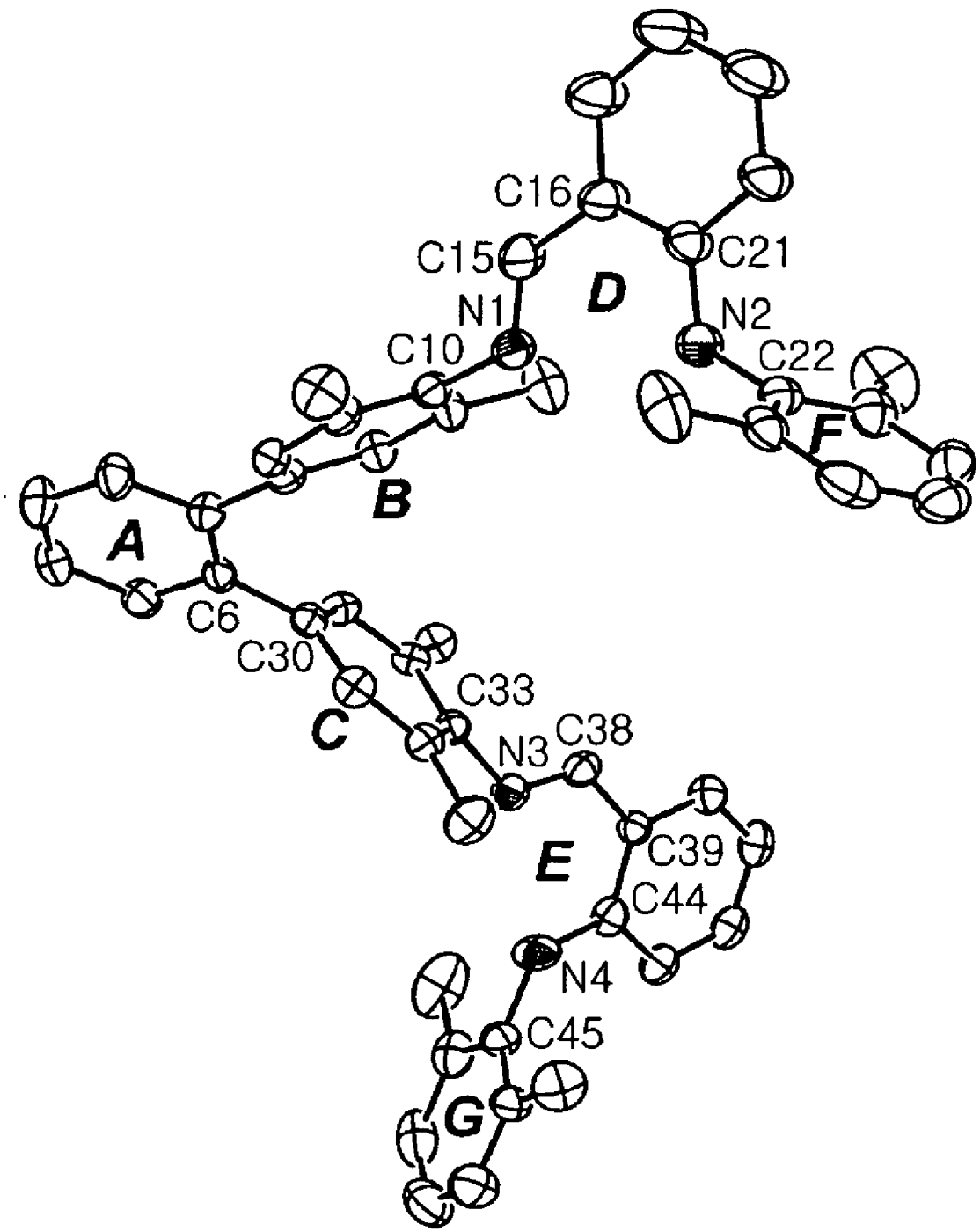
FIG. 1 is an X-ray diffraction diagram of a single crystal of compound (15) according to an embodiment of the present invention.

Hereinafter, the present invention will now be described in more detail.

A catalyst suitable for the bimetallic polymerizing reaction mechanism discovered by Coates, G. W. should have such a structure wherein the centers of two metallic zinc are separated by an appropriated distance. When the polycarbonate is produced from the epoxy compound and carbon dioxide using a single metallic zinc coordinating compound, an appropriate distance between zinc-zinc atoms when two zinc complexes meet each other can be maintained by designing the substituent of the ligand attached to the zinc coordinate compound. However, when the concentration of the catalyst in a polymerization reaction system is low, a probability that the appropriate distance between zinc-zinc atoms is maintained is low. Thus, the polymerization can be efficiently performed only at a high concentration of the single metallic zinc catalyst and a large amount of the catalyst should be used, which is not economical. Since the catalyst can catalyze the reaction at a low ratio of monomer/catalyst, there is a limit to produce a high molecular weight polymer.

The present inventors conducted research to maintain a constant distance between zinc-zinc atoms regardless of the concentration of a catalyst in a polymerization medium and discovered a bimetallic zinc complex having formula 1:

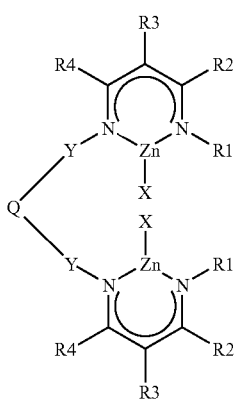

(1)

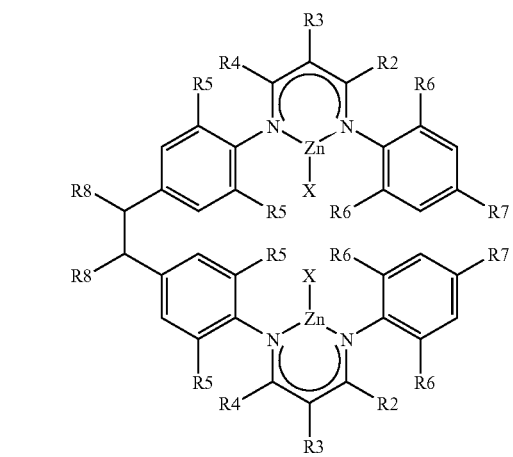

(2)

wherein each of N~N chelate ligands is a monovalent anion and together with zinc forms a 6-membered ring, R1 is a $C_1$-$C_{20}$ alkyl radical having at least one hydrogen atom unsubstituted or substituted by a halogen atom or a $C_6$-$C_{20}$ aryl radical having at least one hydrogen atom unsubstituted or substituted by a halogen atom, and the R1 radicals are either identical or different from each other, R2 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R2 radicals are either identical or different from each other, R3 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R3 radicals are either identical or different from each other, R4 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R4 radicals are either identical or different from each other, either R2 and R3, or R3 and R4 may be linked to each other to form a ring, X is a monovalent anion selected from a $C_1$-$C_{20}$ alkoxy radical having at least one hydrogen atom unsubstituted or substituted by a halogen atom, carboxy, alkylsulfinato, and amido, and the X monovalent anions are either identical or different from each other and each X may be coordinated to only a metallic zinc atom or form a bridged structure between two metallic zinc atoms, Y is a carbon diradical and may have at least one hydrogen substituted by halogen, and the Y diradicals are either identical or different from each other, and Q is a $C_1$-$C_{20}$ alkyl diradical having at least one hydrogen atom unsubstituted or substituted by a halogen atom or a $C_6$-$C_{20}$ aryl diradical having at least one hydrogen atom unsubstituted or substituted by a halogen atom.

An example of the bimetallic zinc complex having formula 1 includes the catalyst having formula 2:

wherein each of N~N chelate ligands is a monovalent anion and together with zinc forms a 6-membered ring, R2 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R2 radicals are either identical or different from each other, R3 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R3 radicals are either identical or different from each other, R4 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R4 radicals are either identical or different from each other, either R2 and R3, or R3 and R4 may be linked to each other to form a ring, R5 is a hydrogen atom or a $C_1$-$C_4$ alkyl radical, and the R5 radicals are either identical or different from each other, R6 is a hydrogen atom or a $C_1$-$C_4$ alkyl radical, and the R6 radicals are either identical or different from each other, R7 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R7 radicals are either identical or different from each other and two R7s may be linked to each other to form a ring, R8 is a hydrogen atom, a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R8 radicals are either identical or different from each other and two R8s may be linked to each other to form a ring, and X is a monovalent anion selected from a $C_1$-$C_{20}$ alkoxy radical having at least one hydrogen atom unsubstituted or substituted by a halogen atom, carboxy, alkylsulfinato, and amido, and the X monovalent anions are either identical or different from each other and each X may be coordinated to only a metallic zinc atom or form a bridged structure between two metallic zinc atoms.

In the catalyst having formula 2, sterical hindrance can be appropriately induced around the zinc atoms by controlling the substituents R5 and R6. Further, an electron effect can be provided to the metals in the center of the catalyst according to an electronic property of the substituent R7.

The catalyst having formula 2 can be synthesized from a β-diketimine compound having formula 3:

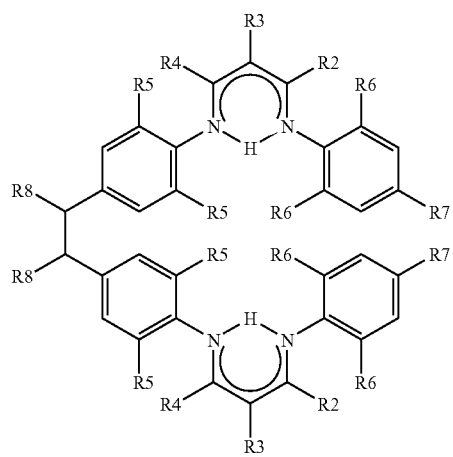

(3)

wherein
R2 through R8 are as described in formula 2.

The synthesis of the compound having formula 2 from the compound having formula 3 includes two methods.

In one method, first, a bimetallic complex of β-diketiminate alkyl zinc or β-diketiminate amido zinc is obtained as an intermediate by reacting the compound having formula 3 with a dialkyl zinc complex or a diamido zinc complex to remove alkane or amine. Then, the resultant bimetallic complex of β-diketiminate alkyl zinc or β-diketiminate amido zinc is reacted with a protic compound having a formula of QH, wherein Q is as described in formula 1, thus obtaining the catalyst having formula 2. The method using the β-diketiminate alkyl zinc complex as an intermediate is described in Moore, D. R. et al., Angew. Chem. Int. Ed. 41, 2599-2602 (2002) and the method using the β-diketiminate amido zinc complex as an intermediate is described in Cheng, M. et al., J. Am. Chem. Soc. 123, 8738-8749 (2002). For example, the compound having formula 1 can be obtained by reacting the bimetallic alkyl zinc complex with an electrically neutral compound, for example, $CO_2$ or $SO_2$ through 1,2-insertion.

In other method, the compound having formula 2 is obtained by dehydrogenating the compound having formula 3 with a base, such as n-butyl lithium and then reacting the dehydrogenated compound with a suitable zinc complex (Cheng, M. et al., J. Am. Chem. Soc. 120, 11018-11019 (1998)).

The compound having formula 2 in which two R8s are linked to each other to form a ring is represented by formula 4:

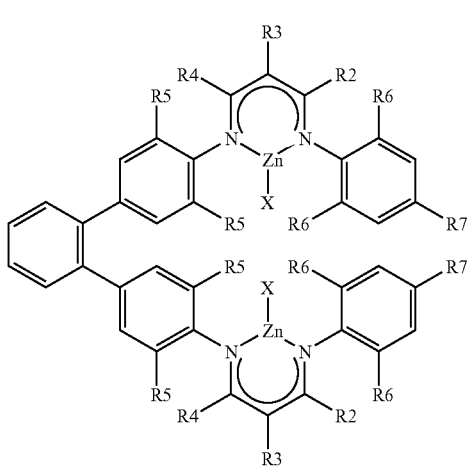

(4)

wherein

R2 through R7 are as described in formula 2.

The bimetallic zinc complex having formula 4 can be produced, for example, according to scheme 1.

In step (a), two aniline moieties are linked to each other via phenylene according to the Suzuki coupling reaction. First, the aniline moieties are protected by reacting with a ketone compound in the presence of a catalyst, and then, after performing the Suzuki coupling reaction, they can be deprotected.

In step (b), two aniline moieties in the compound obtained in the step (a) are converted to a β-diketimine ligand compound through a series of reactions. In this series of reactions, a compound A in which a keto group is introduced into a β-position can be used as an intermediate for the β-diketimine ligand compound. Alternatively, a compound B in which a functional group capable of being substituted with aniline is introduced into a β-position can be used as an intermediate for the β-diketimine ligand compound.

In step (c), the bimetallic zinc complex having formula 4 is obtained through a series of reactions using the metalation method described above.

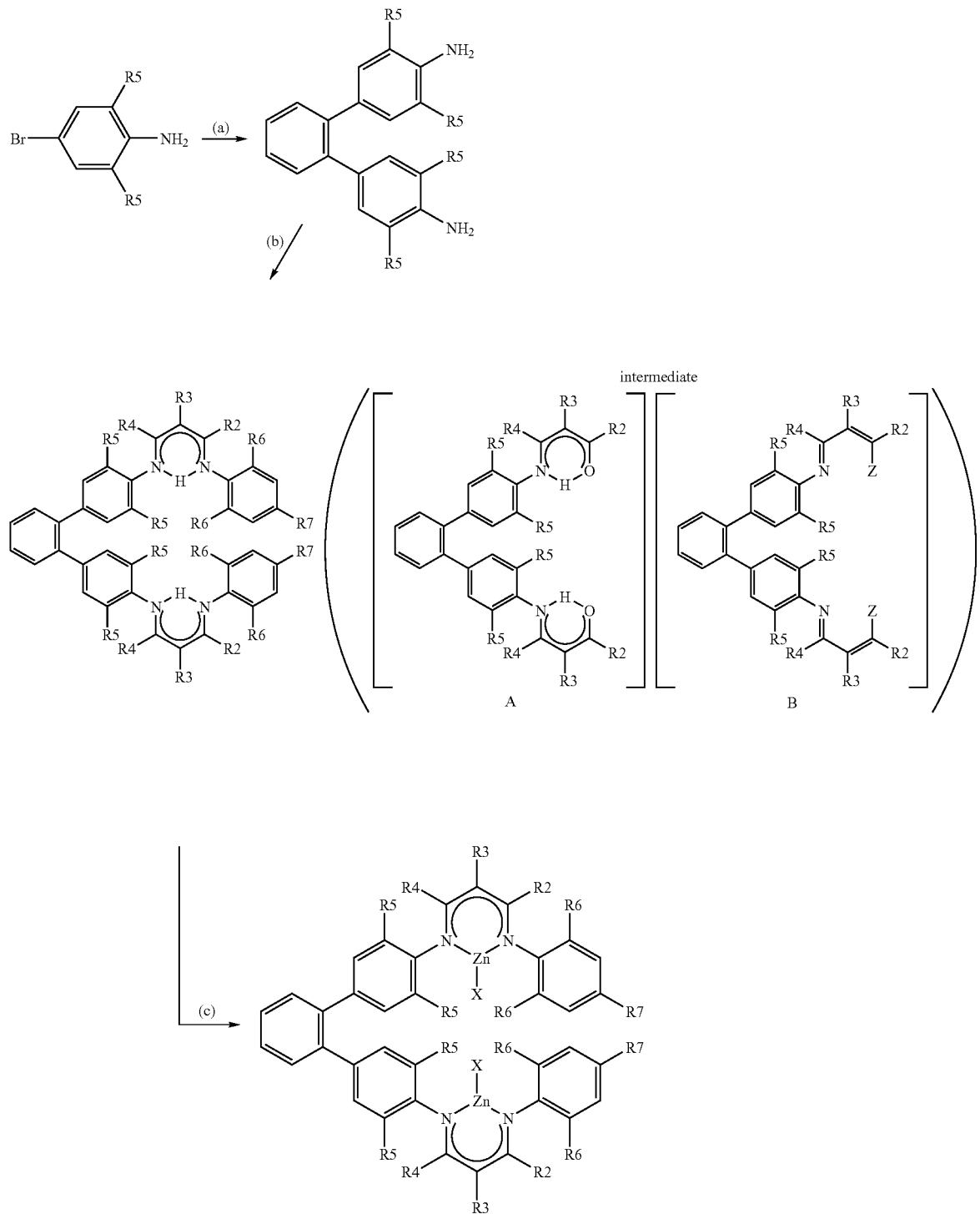
Scheme 1
wherein
R2 through R7 are as described in formula 2,
Z is an atom selected from fluorine, chlorine, bromine, and iodine.
Specific examples of the bimetallic complex according to an embodiment of the present invention include a complex having formula 5 and a complex having formula 6:

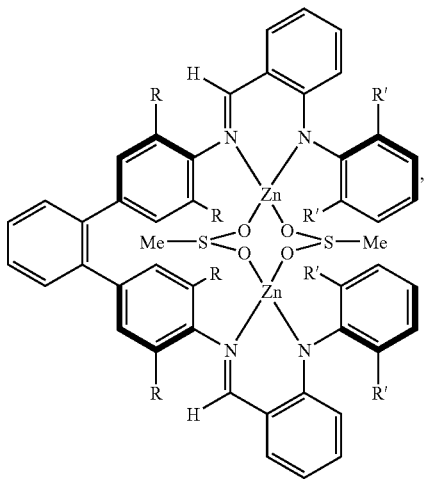

(5)

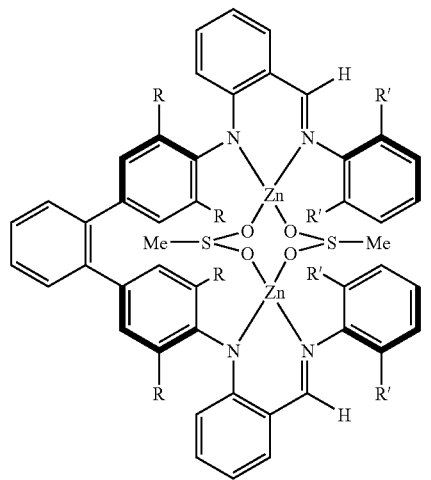

(6)

wherein
each of R and R1 is methyl, ethyl, or isopropyl, and
Me represents methyl.

According to an embodiment of the present invention, polycarbonate may be produced by polymerizing an epoxy compound and carbon dioxide in the presence of the above bimetallic zinc complex as a catalyst.

Since the bimetallic zinc complex having one of formulae 1 through 6 has a structure in which two zinc lingands are bridged via Q, a distance between zinc-zinc atoms is maintained in a limited range regardless of the concentration of the bimetallic zinc complex in a reaction medium for the polymerization of the epoxy compound and carbon dioxide. Thus, a probability that a cooperative operation between active points of two zinc atoms occurs is increased and the bimetallic zinc complex can have a polymerization activity even at a high ratio of monomer/catalyst, thereby reducing a catalyst amount to be used, which is economically advantageous. The bimetallic zinc complex can produce a high molecular weight polymer.

Examples of the epoxy compound used include $C_2$-$C_{20}$ alkylene oxide unsubstituted or substituted by a halogen atom or alkoxy, $C_4$-$C_{20}$ cycloalkene oxide unsubstituted or substituted by a halogen atom or alkoxy, and $C_1$-$C_{10}$ styrene oxide unsubstituted or substituted by a halogen atom, alkoxy, or alkyl.

Specific examples of the epoxy compound include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrin, epichlorohydrin, epibromohydrin, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, α-pinene oxide, 2,3-epoxynorbornene, limonene oxide, dieldrine, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether, etc.

An organic solvent can be used as a reaction medium for the epoxy compound during the polymerization. The organic solvent may include aliphatic hydrocarbon, such as pentane, octane, decane, and cyclohexane; aromatic hydrocarbon, such as benzene, toluene, and xylene; halogenated hydrocarbon, such as chloromethane, methylene chloride, chloroform, carbon tetrachloride, 1,1-dichloroethane, 1,2-dichloroethane, ethyl chloride, trichloroethane, 1-chloropropane, 2-chloropropane, 1-chlorobutane, 2-chlorobutane, 1-chloro-2-methylpropane, chlorobenzene, and bromobenzene. Preferably, bulk polymerization is performed, in which the epoxy compound serves as a solvent.

A volume ratio of the solvent to the epoxy compound is 0:100 to 99:1, preferably 0:100 to 90:1.

A molar ratio of the epoxy compound to the catalyst may be from 100 to 500,000, preferably from 1,000 to 100,000.

The turnover rate of the catalyst, i.e. the mole number of the epoxy compound converted per hour per mole of zinc can be 50 turnover/hr or more.

The pressure of carbon dioxide may be ambient pressure to 100 atm, preferably 2-50 atm. The polymerization temperature may be 20-120° C., preferably 50-100° C.

The polycarbonate may be produced using a polymerization method, such as batch, semi-batch, or continuous polymerization. In the batch or semi-batch polymerization, the reaction time may be 1-24 hours, preferably 1.5-6 hours. Likely, in the continuous polymerization, a mean residence time of the catalyst may be 1-24 hours.

According to an embodiment of the present invention, the polycarbonate having a number average molecular weight (($M_n$)) of 5,000-1,000,000 and a molecular weight distribution ($M_w/M_n$) of 1.05-4.0 may be produced. The term "number average molecular weight ($M_n$)" refers to a number average molecular weight measured by gel permeation chromatography (GPC), calibrating with polystyrene having a single distribution of molecular weight as a standard material. The term "molecular weight distribution ($M_w/(M_n)$)" refers to a ratio of a weight average molecular weight to a number average molecular weight, wherein the weight average molecular weight is measured by GPC in the same manner as ($M_n$).

The polycarbonate is composed of at least 85% carbonate bond, and often at least 92% carbonate bond. Said polycarbonate is easily biodegradable and useful as, for example, packages or coating materials.

Hereinafter, the present invention will be described in more detail with reference to the following examples. However, these examples are provided for the purpose of illustration and are not intended to limit the scope of the invention.

EXAMPLES

Example 1

Synthesis of N-diphenylmethylene-2,6-diisopropyl-4-bromoaniline (compound (1))

40.7 g (0.195 mol) of tetraethoxysilane and 0.5 mL of sulfuric acid were added to a flask equipped with a distiller, containing 43.9 g (0.169 mol) of 4-bromo-2,6-diisopropylaniline and 24.8 g (0.130 mol) of benzophenone under a nitrogen atmosphere. The mixture was reacted by heating at 160° C. for 2 days while removing formed ethanol using the distiller. After the reaction, the resultant product was cooled to room temperature. Then, 200 mL of 1.0 M aqueous solution of potassium hydroxide was added to the resultant product and stirred for 10 minutes to obtain yellow precipitates. The obtained precipitates were filtered off and dissolved in 300 mL of ethyl acetate, and then dried over anhydrous magnesium sulfate. The solvent was removed by distillation under reduced pressure to obtain a yellow solid. Then, the yellow solid was recrystallized in hexane at −20° C. to obtain 42 g of N-diphenylmethylene-2,6-diisopropyl-4-bromoaniline compound.

Yield 77%. M.p. 114° C. IR (KBr): 1620 (C=N) cm$^{-1}$. $^1$H NMR (CDCl$_3$): δ 7.76 (d, J=7.6 Hz, 2H, o-H), 7.43 (t, J=6.4 Hz, 1H, p-H), 7.37 (t, J=6.4 Hz, 2H, m-H), 7.20 (t, J=6.4 Hz, 1H, p-H), 7.18 (t, J=7.6 Hz, 2H, m-H), 7.05 (s, 2H), 7.04 (d, J=7.6 Hz, 2H, o-H), 2.83 (septet, J=7.2 Hz, 2H, CH), 1.11 (d, J=7.2 Hz, 6H, CH$_3$), 0.91 (d, J=7.2 Hz, 6H, CH$_3$) ppm. $^{13}$C{$^1$H} NMR(CDCl$_3$): δ 166.61, 145.74, 139.71, 138.43, 135.93, 130.75, 129.63, 129.31, 129.11, 128.38, 128.02, 126.09, 116.73, 28.99, 24.34, 22.12 ppm. Anal. Calc. (C$_{25}$H$_{26}$BrN): C, 71.43; H, 6.23; N, 3.33%. Found: C, 71.41; H, 6.25; N, 3.24%.

Example 2

Synthesis of N-diphenylmethylene-2,6-diethyl-4-bromoaniline (compound (2))

N-diphenylmethylene-2,6-diethyl-4-bromoaniline was synthesized using the same manner as in Example 1, except that 4-bromo-2,6-diethylaniline was used in place of 4-bromo-2,6-diisopropylaniline.

Yield 75%. M.p. 112° C. IR (KBr): 1612 (C=N) cm$^{-1}$. $^1$H NMR (CDCl$_3$): δ 7.74 (d, J=8.0 Hz, 2H, o-H), 7.44 (t, J=7.2 Hz, 1H, p-H), 7.37 (t, J=7.2 Hz, 2H, m-H), 7.21 (t, J=7.6 Hz, 1H, p-H), 7.17 (t, J=7.6 Hz, 2H, m-H), 7.04 (d, J=8.0 Hz, 2H, o-H), 7.03 (s, 2H), 2.47 (dq, J=15.2, 7.6 Hz, 2H, CH$_2$), 2.21 (dq, J=15.2, 7.6 Hz, 2H, CH$_2$), 1.09 (t, J=7.2 Hz, 6H, CH$_3$) ppm. $^{13}$C{$^1$H} NMR(CDCl$_3$): δ 167.08, 147.09, 139.63, 136.35, 133.73, 130.85, 129.57, 129.40, 128.67, 128.37, 128.06, 125.54, 116.09, 24.96 (CH$_2$), 13.69 (CH$_3$) ppm. Anal. Calc. (C$_{23}$H$_{22}$BrN): C, 70.41; H, 5.65; N, 3.57%. Found: C, 70.34; H, 5.44; N, 3.49%.

Example 3

Synthesis of N-diphenylmethylene-2,6-dimethyl-4-bromoaniline (compound (3))

N-diphenylmethylene-2,6-dimethyl-4-bromoaniline (compound (3)) was synthesized using the same manner as in Example 1, except that 4-bromo-2,6-dimethylaniline was used in place of 4-bromo-2,6-diisopropylaniline.

Yield 59%. M.p. 88° C. IR (KBr): 1616 (C=N) cm$^{-1}$. $^1$H NMR (CDCl$_3$): δ 7.74 (d, J=7.2 Hz, 2H, o-H), 7.42 (t, J=7.2 Hz, 1H, p-H), 7.35 (t, J=7.6 Hz, 2H, m-H), 7.23 (t, J=7.2 Hz, 1H, p-H), 7.17 (t, J=7.2 Hz, 2H, m-H), 7.05 (d, J=7.6 Hz, 2H, o-H), 6.98 (s, 2H), 1.99 (s, 6H, CH$_3$) ppm. $^{13}$C{$^1$H} NMR(CDCl$_3$): δ 167.96, 148.20, 139.58, 136.74, 130.99, 130.48, 129.59, 129.52, 128.50, 128.43, 128.27, 128.15, 115.43, 18.85 (CH$_3$) ppm. Anal. Calc. (C$_{21}$H$_{18}$BrN): C, 69.24; H, 4.98; N, 3.85%. Found: C, 69.03; H, 5.08; N, 3.74%.

Compounds (1) through (3) have the following formulae, respectively.

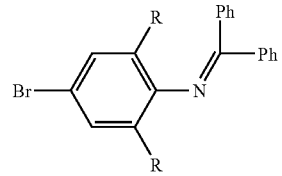

| Compound | 1 | 2 | 3 |
| --- | --- | --- | --- |
| R | iPr | Et | Me |

Example 4

Synthesis of N-diphenylmethylene-2,6-diisopropyl-4-dihydroxyboro-aniline (compound (4))

20.0 g (47.8 mmol) of compound (1) obtained in Example 1 was dissolved in 500 mL of tetrahydrofuran and a 2.5 M hexane solution of 13.25 g (47.8 mmol) of n-butyl lithium was added dropwise to the solution at −78° C. Then, 8.99 g (47.8 mmol) of triisopropyl boronate (B(OiPr)$_3$) was added to the resultant solution at −78° C. for 2 hours using a syringe. Subsequently, the reactant solution was warmed to room temperature and stirred for 15 hours. The resultant solution was poured into a separatory funnel containing 500 mL of an aqueous solution of ammonium chloride and violently shaken for 5 minutes. 500 mL of diethyl ether was added to the obtained solution and shaken, and then, an organic layer was separated and collected. The collected organic layer was dried over anhydrous magnesium sulfate and the solvent was removed by distillation under reduced pressure. The residual was treated with hexane to obtain N-diphenylmethylene-2,6-diisopropyl-4-dihydroxyboro-aniline as light yellow solid powders (16.0 g).

Yield 87%. IR (KBr): 3425 (br, O—H), 1604 (C=N) cm$^{-1}$. $^1$H NMR (CDCl$_3$): δ 7.88 (s, 2H), 7.94-7.68 (br, 2H), 7.54-7.28 (br, 4H), 7.28-6.98 (br, 6H), 2.93 (septet, J=7.2 Hz, 2H, CH), 1.38-0.96 (br, 12H, CH$_3$) ppm. $^{13}$C{$^1$H} NMR(CDCl$_3$): δ 165.44, 150.82, 139.65 (br), 135.98 (br), 135.17, 130.48, 130.5-127.5 (m), 124.89 (br), 28.86, 24.32 (br), 22.20 (br) ppm.

Example 5

Synthesis of N-diphenyl methylene-2,6-diethyl-4-dihydroxyboro-aniline (compound (5))

N-diphenylmethylene-2,6-diethyl-4-dihydroxyboro-aniline (compound (5)) was synthesized using the same manner as in Example 4, except that compound (2) obtained in Example 2 was used in place of compound (1).

Yield 82%. IR (KBr): 3425 (br, O—H), 1605 (C=N) cm$^{-1}$. $^1$H NMR (CDCl$_3$): δ 7.80 (s, 2H), 7.90-7.70 (br, 2H), 7.54-7.31 (br, 4H), 7.29-6.98 (br, 6H), 2.68-2.45 (br, 2H, CH$_2$), 2.45-2.22 (br, 2H, CH$_2$), 1.23 (t, J=7.2 Hz, 6H, CH$_3$) ppm. $^{13}$C{$^1$H} NMR(CDCl$_3$): δ 165.84, 152.10, 139.67 (br), 136.34 (br), 133.20, 130.74, 130.5-127.5, 124.52 (br), 25.07, 13.77 ppm.

Example 6

Synthesis of N-diphenylmethylene-2,6-dimethyl-4-dihydroxyboro-aniline (compound (6))

N-diphenylmethylene-2,6-dimethyl-4-dihydroxyboro-aniline (compound (6)) was synthesized using the same manner as in Example 4, except that compound (3) obtained in Example 3 was used in place of compound (1).

Yield 82%. IR (KBr): 3425 (br, O—H), 1605 (C=N) cm$^{-1}$. $^1$H NMR (CDCl$_3$): δ 7.82-7.75 (br, 2H), 7.73 (s, 2H), 7.40-7.34 (br, 4H), 7.26-7.04 (br, 6H), 2.14 (s, 6H) ppm. $^{13}$C{$^1$H} NMR(CDCl$_3$): δ 166.85, 153.14, 139.60 (br), 136.75 (br), 135.49, 130.85 (br), 129.60 (br), 129.55 (br), 128.57 (br), 128.38 (br), 127.99 (br), 125.49, 124.50 (br), 18.94 ppm.

Compounds (4) through (6) have the following formulae, respectively.

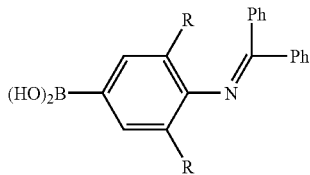

| Compound | 4 | 5 | 6 |
|---|---|---|---|
| R | iPr | Et | Me |

Example 7

Synthesis of 1,2-phenylenebis-4-(2,6-diisopropylaniline) (compound (7))

16.8 g (43.9 mmol) of compound (4) obtained in Example 4, 12.7 g (120 mmol) of sodium carbonate, and 0.69 g (0.60 mmol) of tetrakisphosphino palladium were added to a Schrenk flask installed in a glovebox. The flask was removed from the glovebox and 220 mL of deaerated dimethoxyethane, 55 mL of deaerated distilled water, and 2.37 mL (20.0 mmol) of 1,2-dibromobenzene were added to the flask. Then, the flask was sealed and stirred at 100° C. for 15 hours. The resultant product was cooled to room temperature and a yellow solid was precipitated. The yellow precipitates were filtered and collected, and then washed with distilled water. 100 mL of tetrahydrofuran and 50 mL of 2 N hydrochloric acid were added to the resultant product and stirred at 60° C. for 3 hours and distilled under reduced pressure to obtain a white solid. The white solid was washed with diethyl ether to completely remove benzophenone formed as a side product. 100 mL of diethyl ether and 150 mL of a 1.0 N aqueous solution of potassium hydroxide were added and an organic layer was separated and collected using a separatory funnel. A separated aqueous layer was extracted with 100 mL of diethyl ether and collected, and then, dried over anhydrous magnesium sulfate. The solvent was removed by distillation under reduced pressure to obtain a pure white crystalline solid, determined by NMR.

Yield 7.00 g (82%). M.p. 178° C. IR (KBr): 3481 and 3385 (N—H) cm$^{-1}$. $^1$H NMR (CDCl$_3$): δ 7.44 (AA'BB', 1H, H-2), 7.31 (AA'BB', 1H, H-1), 6.74 (s, 2H, H-3), 3.56 (br, 2H, NH), 2.79 (septet, J=6.4 Hz, 2H, CH), 1.06 (d, J=6.4 Hz, 12H, CH$_3$) ppm. $^{13}$C{$^1$H} NMR(CDCl$_3$): δ 142.07, 138.57, 132.16, 132.05, 130.01, 126.84, 124.99, 28.21 (CH$_3$), 22.91 (CH) ppm. Anal. Calc. (C$_{30}$H$_{40}$N$_2$): C, 84.06; H, 9.41; N, 6.54%. Found: C, 83.76; H, 9.52; N, 6.46%.

Example 8

Synthesis of 1,2-phenylenebis-4-(2,6-diethylaniline) (compound (8))

Compound (8) was synthesized using the same manner as in Example 7, except that compound (5) obtained in Example 5 was used in place of compound (4). In this case, an imine compound, which is an intermediate during the Suzuki coupling, was not precipitated and was extracted with ethyl acetate, and purified by silica gel column chromatography using toluene as an elution solution. The subsequent reactions and work-up were performed in the same manner as in the Example 7.

Yield 75%. M.p. 118° C. IR (KBr): 3479 and 3396 (N—H) cm$^{-1}$. $^1$H NMR (CDCl$_3$): δ 7.39 (AA'BB', 1H, H-2), 7.28 (AA'BB', 1H, H-1), 6.71 (s, 2H, H-3), 3.49 (br, 2H, NH), 2.38 (q, J=7.6 Hz, 4H, CH$_2$), 1.05 (d, J=7.6 Hz, 6H, CH$_3$) ppm. $^{13}$C{$^1$H} NMR(CDCl$_3$): δ 141.33, 139.93, 132.07, 130.25, 127.97, 127.27, 126.78, 24.63 (CH$_2$), 12.52 (CH$_3$) ppm. Anal. Calc. (C$_{26}$H$_{32}$N$_2$): C, 83.82; H, 8.66; N, 7.52%. Found: C, 83.47; H, 8.75; N, 7.49%.

Example 9

Synthesis of 1,2-phenylenebis-4-(2,6-diethylaniline) (compound (9))

Compound (9) was synthesized using the same manner as in Example 8, except that compound (6) obtained in Example 6 was used in place of compound (5).

Yield 85%. M.p. 138° C. IR (KBr): 3440 and 3363 (N—H) cm$^{-1}$. $^1$H NMR (CDCl$_3$): δ 7.46 (AA'BB', 1H, H-2), 7.39 (AA'BB', 1H, H-1), 6.90 (s, 2H, H-3), 3.56 (br, 2H, NH), 2.18 (s, 6H, CH$_3$) ppm. $^{13}$C{$^1$H} NMR(CDCl$_3$): δ 141.34, 140.78, 132.06, 130.86, 129.98, 126.74, 121.34, 38.18 (CH$_3$) ppm. Anal. Calc. (C$_{22}$H$_{24}$N$_2$): C, 83.50; H, 7.64; N, 8.85%. Found: C, 83.36; H, 7.79; N, 8.71%.

Compounds (7) through (9) have the following formulae, respectively.

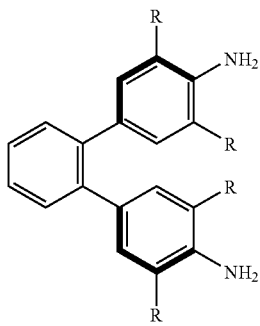

| Compound | 7 | 8 | 9 |
|---|---|---|---|
| R | iPr | Et | Me |

Example 10

Synthesis of 1,2-phenylenebis-4-(N-(o-fluorophenylmethylene)-2,6-diisopropylaniline) (compound (10))

1.00 g (2.33 mmol) of compound (7) obtained in Example 7, 1.16 g (9.33 mmol) of 2-fluorobenzaldehyde, and 45 mg (0.23 mmol) of p-toluene sulfonic acid were dissolved in 50 mL of toluene in a flask. A dehydration reaction was performed for 1 day using a Dean-star apparatus and after 0.58 g (4.7 mmol) of 2-fluorobenzaldehyde and 23 mg (0.12 mmol) of p-toluene sulfonic acid were further added, the reaction was continued for 1 day. After the reaction was completed, the resultant product was cooled to room temperature and 50 mL of a saturated sodium bicarbonate solution was added, and then an organic layer was separated and collected. A separated aqueous layer was extracted with 50 mL of ethyl acetate three times. The collected organic layer was dried over anhydrous magnesium sulfate and the solvent was removed by distillation under reduced pressure. The obtained residue was purified by silica gel column chromatography using a mixed solvent of hexane:ethyl acetate=10:1 as an elution solution to obtain 1.30 g of 1,2-phenylenebis-4-(N-(o-fluorophenylmethylene)-2,6-diisopropylaniline).

Yield 87%. M.p. 127° C. IR (NaCl): 1633 (C=N) cm$^{-1}$. $^1$H NMR (CDCl$_3$): δ 8.41 (s, 1H, H-4), 8.18 (td, J=7.6, 1.2 Hz, 1H, H-7), 7.51 (AA'BB', 1H, H-2), 7.48-7.42 (m, 1H), 7.40 (AA'BB', 1H, H-1), 7.23 (t, J=8.0 Hz, 1H), 7.10 (t, J=9.2 Hz, 1H), 6.92 (s, 2H), 2.86 (septet, J=6.8 Hz, 2H, CH), 1.02 (d, J=6.8 Hz, 12H, CH$_3$) ppm. $^{13}$C{$^1$H} NMR(CDCl$_3$): δ 162.57 (d, J=251 Hz, C—F), 155.27 (d, J=4.5 Hz, C=N), 147.51, 141.43, 137.36, 136.91, 132.72 (d, J=7.6 Hz), 129.92, 127.56 (d, J=2.0 Hz), 126.96, 124.86, 124.37 (d, J=3.8 Hz), 123.71 (d, J=9.1 Hz), 115.70 (d, J=20.4 Hz), 27.86 (CH$_3$), 23.61 (CH) ppm. Anal. Calc. (C$_{44}$H$_{46}$F$_2$N$_2$): C, 82.46; H, 7.24; N, 4.37. Found: C, 82.60; H, 7.37; N, 4.34%.

Example 11

Synthesis of 1,2-phenylenebis-4-(N-(o-fluorophenylmethylene)-2,6-diethylaniline) (compound (11))

Compound (11) was synthesized using the same manner as in Example 10, except that compound (8) obtained in Example 8 was used in place of compound (7).

Yield 75%. M.p. 112° C. IR (NaCl): 1635 (C=N) cm$^{-1}$. $^1$H NMR (CDCl$_3$): δ 8.48 (s, 1H, C(=N)H), 8.21 (td, J=7.6, 1.2 Hz, 1H), 7.51 (AA'BB', 1H, H-2), 7.48-7.42 (m, 1H), 7.40 (AA'BB', 1H, H-1), 7.26 (t, J=7.2 Hz, 1H), 7.12 (t, J=8.8 Hz, 1H), 6.91 (s, 2H), 2.42 (q, J=7.2 Hz, 4H, CH$_2$), 1.02 (d, J=7.2 Hz, 6H, CH$_3$) ppm. $^{13}$C{$^1$H} NMR(CDCl$_3$): δ 162.54 (d, J=251 Hz, C—F), 155.41 (d, J=5.3 Hz, C=N), 148.72, 140.74, 137.24, 132.73 (d, J=8.4 Hz), 132.39, 130.01, 127.87, 127.50 (d, J=2.2 Hz), 126.95, 124.35 (d, J=4.2 Hz), 123.69 (d, J=9.1 Hz), 115.75 (d, J=20.5 Hz), 24.64 (CH$_2$), 14.88 (CH$_3$) ppm. Anal. Calc. (C$_{40}$H$_{38}$F$_2$N$_2$): C, 82.16; H, 6.55; N, 4.79. Found: C, 82.02; H, 6.54; N, 4.82%.

Example 12

Synthesis of 1,2-phenylenebis-4-(N-(o-fluorophenylmethylene)-2,6-dimethylaniline) (compound (12))

Compound (12) was synthesized using the same manner as in Example 10, except that compound (9) obtained in Example 9 was used in place of compound (7).

Yield 73%. M.p. 128° C. IR (NaCl): 1635 (C=N) cm$^{-1}$. $^1$H NMR (CDCl$_3$): δ 8.50 (s, 1H, C(=N)H), 8.20 (td, J=7.2, 2.0 Hz, 1H, H-2), 7.46-7.38 (m, 2H), 7.34 (AA'BB', 1H, H-1), 7.23 (t, J=7.2 Hz, 1H), 7.09 (t, J=8.8 Hz, 1H), 6.90 (s, 2H), 2.07 (s, 6H, CH$_3$) ppm. $^{13}$C{$^1$H} NMR(CDCl$_3$): δ 162.53 (d, J=251 Hz, C—F), 156.10 (d, J=4.6 Hz, C=N), 149.50, 140.14, 137.15, 132.80 (d, J=8.3 Hz), 130.38, 129.48, 127.43 (d, J=3.1 Hz), 126.87, 126.30, 124.33 (d, J=3.0 Hz), 123.63 (d, J=9.1 Hz), 115.80 (d, J=20.5 Hz), 18.44 (CH$_3$) ppm. Anal. Calc. (C$_{36}$H$_{30}$F$_2$N$_2$): C, 81.79; H, 5.72; N, 5.30. Found: C, 81.69; H, 5.98; N, 5.33%.

Compounds (10) through (12) have the following formulae, respectively.

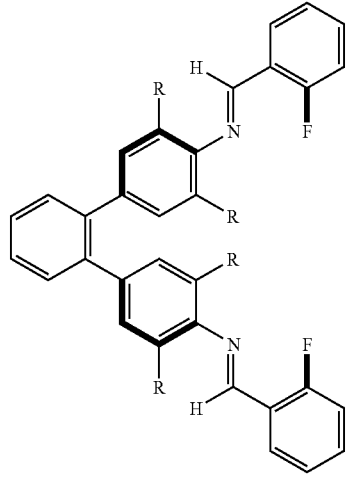

| Compound | 10 | 11 | 12 |
|---|---|---|---|
| R | iPr | Et | Me |

Element numbers indicated in NMR spectrum data of ligand precursor compounds produced in the following Examples are according to the numbers defined in the following formulae. Similarly, element numbers indicated in NMR spectrum data of bimetallic complexes, which are coordinated to zinc by dehydrogenating the ligand precursor compounds, are according to the numbers defined in the following formulae.

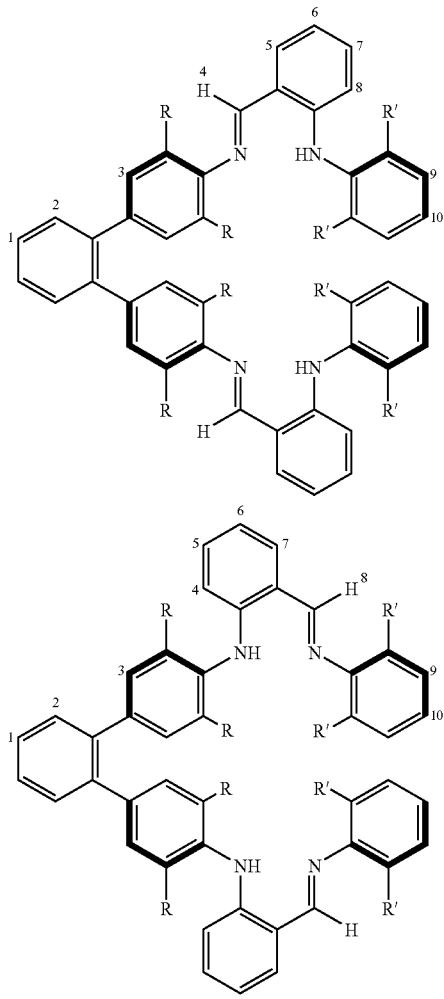

Example 13

Synthesis of 1,2-phenylenebis-4-(N-(o-(2,6-diisopropylphenylamino)phenylmethylene)-2,6-diisopropylaniline) (compound (13))

0.500 g (0.783 mmol) of compound (10) obtained in Example 10 and 2,6-diisopropylaniline were treated with n-butyl lithium in a solution of tetrahydrofuran at −78° C. to obtain 1.42 g (7.83 mmol) of lithium salt of 2,6-diisopropylaniline, which was placed into a flask replaced by nitrogen. The flask was cooled to −20° C. and 7 mL of tetrahydrofuran cooled to −20° C. was added to the flask, and then the resultant solution was stirred for 15 hours. The reaction was stopped by adding 20 mL of distilled water and the resultant organic product was extracted with 20 mL of ethyl acetate three times. The collected organic solution was dried over anhydrous magnesium sulfate and distilled under reduced pressure to obtain an oily residue. The oily residue was treated with hexane to obtain 1,2-phenylenebis-4-(N-(o-(2,6-diisopropylphenylamino)phenyl methylene)-2,6-diisopropylaniline) (compound (13)) as powders (0.640 g).

Yield 86%. M.p. 234° C. IR (NaCl): 3188 (N—H), 1622 (C=N) cm$^{-1}$. $^1$H NMR (C$_6$D$_6$): δ 10.79 (s, 1H, N—H), 8.33 (s, 1H, H-4), 7.65 (AA'BB', 1H, H-2), 7.33 (AA'BB', 1H, H-1), 7.30-7.18 (A2B, 3H, H-9 and H-10), 7.15 (d, J=6.8 Hz, 1H, H-5), 7.13 (s, 2H, H-3), 6.96 (t, J=7.2 Hz, 1H, H-7), 6.73 (t, J=7.2 Hz, 1H, H-6), 6.39 (d, J=8.4 Hz, 1H, H-8), 3.37 (septet, J=6.8 Hz, 2H, CH), 3.22 (septet, J=6.8 Hz, 2H, CH), 1.14 (d, J=6.8 Hz, 12H, CH$_3$), 1.12 (d, J=6.8 Hz, 12H, CH$_3$) ppm. $^{13}$C{$^1$H} NMR(C$_6$D$_6$): δ 166.28, 150.40, 147.66, 147.44, 142.25, 138.49, 138.00, 134.90, 134.86, 132.63, 130.40, 127.58, 125.58, 124.25, 116.80, 115.92, 112.35, 29.17 (CH$_3$), 28.61 (CH$_3$), 25.23 (CH$_3$), 24.05 (CH), 23.20 (CH) ppm. Anal. Calc. (C$_{68}$H$_{82}$N$_4$): C, 85.48; H, 8.65; N, 5.86. Found: C, 85.25; H, 8.76; N, 5.80%.

Example 14

Synthesis of 1,2-phenylenebis-4-(N-(o-(2,6-diethylphenylamino)phenylmethylene)-2,6-diethylaniline) (compound (14))

1,2-phenylenebis-4-(N-(o-(2,6-diethylphenylamino)phenylmethylene)-2,6-diethylaniline) (compound (14)) was produced using the same manner as in Example 13, except that compound (11) obtained in Example 11 was used in place of compound (10).

Yield 88%. M.p. 137° C. IR (NaCl): 3188 (N—H), 1622 (C=N) cm$^{-1}$. $^1$H NMR (CDCl$_3$): δ 10.48 (s, 1H, N—H), 8.29 (s, 1H, H-4), 7.48 (AA'BB', 1H, H-2), 7.37 (AA'BB', 1H, H-1), 7.26 (d, J=7.6 Hz, 1H, H-5), 7.23-7.13 (A2B, 3H, H-9 and H-10), 7.11 (t, J=8.0 Hz, 1H, H-7), 6.89 (s, 2H, H-3), 6.66 (t, J=7.2 Hz, 1H, H-6), 6.24 (d, J=7.6 Hz, 1H, H-8), 2.62 (dq, J=14.4, 7.6 Hz, 2H, CH$_2$), 2.53 (dq, J=14.4, 7.6 Hz, 2H, CH$_2$), 2.45 (q, J=7.6 Hz, 4H, CH$_2$), 1.10 (t, J=7.6 Hz, 6H, CH$_3$), 1.00 (t, J=7.6 Hz, 6H, CH$_3$) ppm. $^{13}$C{$^1$H} NMR(CDCl$_3$): δ 165.61, 148.92, 148.10, 142.66, 140.71, 140.25, 135.89, 134.29, 133.08, 131.95, 129.94, 127.00, 126.99, 126.83, 126.68, 116.35, 115.12, 111.72, 25.19 (CH$_2$), 24.83 (CH$_2$), 15.17 (CH$_3$), 15.05 (CH$_3$) ppm. Anal. Calc. (C$_{60}$H$_{66}$N$_4$): C, 85.47; H, 7.89; N, 6.64. Found: C, 85.79; H, 8.22; N, 6.73%.

Example 15

Synthesis of 1,2-phenylenebis-4-(N-(o-(2,6-dimethylphenylamino)phenylmethylene)-2,6-dimethylaniline) (compound (15))

1,2-phenylenebis-4-(N-(o-(2,6-dimethylphenylamino) phenylmethylene)-2,6-dimethylaniline) (compound (15)) was produced using the same manner as in Example 13, except that compound (12) obtained in Example 12 was used in place of compound (10).

Yield 94%. M.p. 220° C. IR (NaCl): 3188 (N—H), 1622 (C=N) cm$^{-1}$. $^1$H NMR (C$_6$D$_6$): δ 10.50 (s, 1H, N—H), 7.94 (s, 1H, H-4), 7.56 (AA'BB', 1H, H-2), 7.32 (AA'BB', 1H, H-1), 7.19 (s, 2H, H-3), 7.08-6.98 (m, 4H, H-9, H-10 and H-5), 6.94 (t, J=7.6 Hz, 1H, H-7), 6.58 (t, J=6.8 Hz, 1H, H-6), 6.32 (d, J=8.0 Hz, 1H, H-8), 2.12 (s, 6H, CH$_3$), 2.06 (s, 6H, CH$_3$) ppm. $^{13}$C{$^1$H} NMR(C$_6$D$_6$): δ 166.35, 149.94, 148.85, 141.27, 138.28, 137.96, 137.03, 135.00, 132.52, 131.32, 130.09, 128.69, 127.49, 127.36, 126.72, 117.20, 115.81, 111.99, 19.03 (CH$_3$), 18.65 (CH$_3$) ppm. Anal. Calc. (C$_{52}$H$_{50}$N$_4$): C, 85.44; H, 6.89; N, 7.66. Found: C, 85.27; H, 7.21; N, 7.40%.

An X-ray diffraction structure of a single crystal of compound (15) produced in Example 15 was found. The chemical structure of compound (15) is shown in FIG. 1.

Example 16

Synthesis of 1,2-phenylenebis-4-(N-(o-(2,6-dimethylphenylamino)phenylmethylene)-2,6-diisopropylaniline) (compound (16))

1,2-phenylenebis-4-(N-(o-(2,6-dimethylphenylamino)phenylmethylene)-2,6-diisopropylaniline) (compound (16)) was produced using the same manner as in Example 13, except that compound (12) obtained in Example 12 was used in place of compound (10).

Yield 93%. M.p. 176° C. IR (NaCl): 3188 (N—H), 1622 (C=N) cm$^{-1}$. $^1$H NMR (C$_6$D$_6$): δ 10.77 (s, 1H, N—H), 7.98 (s, 1H, H-4), 7.57 (AA'BB', 1H, H-2), 7.32 (AA'BB', 1H, H-1), 7.30-7.15 (A2B, 3H, H-9 and H-10), 7.18 (s, 2H, H-3), 7.03 (d, J=7.6 Hz, 1H, H-5), 6.96 (t, J=7.2 Hz, 1H, H-7), 6.58 (t, J=7.2 Hz, 1H, H-6), 6.39 (d, J=8.0 Hz, 1H, H-8), 3.32 (septet, J=6.8 Hz, 2H, CH), 2.11 (s, 6H, CH$_3$), 1.10 (d, J=6.8 Hz, 6H, CH$_3$), 1.09 (d, J=6.8 Hz, 6H, CH$_3$) ppm. $^{13}$C{$^1$H} NMR(C$_6$D$_6$): δ 166.52, 150.37, 149.86, 147.67, 141.17, 138.20, 135.13, 134.89, 132.49, 131.23, 130.18, 127.45, 124.20, 116.87, 115.70, 112.40, 29.11 (CH$_3$), 25.02 (CH), 23.35 (CH$_3$), 18.90 (CH$_3$) ppm. Anal. Calc. (C$_{60}$H$_{66}$N$_4$): C, 85.47; H, 7.89; N, 6.64. Found: C, 85.54; H, 8.20; N, 6.48%.

Example 17

Synthesis of 1,2-phenylenebis-4-(N-(o-(2,6-diethylphenylamino)phenylmethylene)-2,6-dimethylaniline) (compound (17))

1,2-phenylenebis-4-(N-(o-(2,6-diethylphenylamino)phenylmethylene)-2,6-dimethylaniline) (compound (17)) was produced using the same manner as in Example 13, except that compound (11) obtained in Example 11 was used in place of compound (10).

Yield 93%. M.p. 182° C. IR (NaCl): 3188 (N—H), 1622 (C=N) cm$^{-1}$. $^1$H NMR (CDCl$_3$): δ 10.49 (s, 1H, N—H), 8.29 (s, 1H, H-4), 7.48 (AA'BB', 1H, H-2), 7.37 (AA'BB', 1H, H-1), 7.27 (d, J=7.6 Hz, 1H, H-5), 7.17-7.05 (m, 4H, H-7, H-9 and H-10), 6.89 (s, 2H, H-3), 6.68 (t, J=7.2 Hz, 1H, H-6), 6.24 (d, J=7.6 Hz, 1H, H-8), 2.45 (q, J=7.2 Hz, 4H, CH$_2$), 2.21 (s, 6H, CH$_3$), 0.98 (t, J=7.2 Hz, 6H, CH$_3$) ppm. $^{13}$C{$^1$H} NMR (CDCl$_3$): δ 165.39, 148.21, 148.04, 140.68, 137.23, 136.59, 134.35, 133.01, 132.00, 129.97, 128.22, 128.03, 126.98, 126.23, 116.53, 111.20, 111.56, 24.93 (CH$_2$), 18.43 (CH$_3$), 15.02 (CH$_3$) ppm. Anal. Calc. (C$_{56}$H$_{58}$N$_4$): C, 85.45; H, 7.46; N, 7.12. Found: C, 85.78; H, 7.79; N, 7.17%.

Example 18

Synthesis of 1,2-phenylenebis-4-(N-(o-(2,6-diethylphenylamino)phenylmethylene)-2,6-diisopropylaniline) (compound (18))

1,2-phenylenebis-4-(N-(o-(2,6-diethylphenylamino)phenylmethylene)-2,6-diisopropylaniline) (compound (18)) was produced using the same manner as in Example 13, except that compound (12) obtained in Example 12 was used in place of compound (10).

Yield 90%. M.p. 202° C. IR (NaCl): 3197 (N—H), 1622 (C=N) cm$^{-1}$. $^1$H NMR (CDCl$_3$): δ 10.44 (s, 1H, N—H), 8.29 (s, 1H, H-4), 7.48 (AA'BB', 1H, H-2), 7.37 (AA'BB', 1H, H-1), 7.32-7.16 (A2B, 3H, H-9 and H-10), 7.20 (d, J=7.6 Hz, 1H, H-5), 7.11 (t, J=7.6 Hz, 1H, H-7), 6.88 (s, 2H, H-3), 6.64 (t, J=7.2 Hz, 1H, H-6), 6.24 (d, J=8.4 Hz, 1H, H-8), 3.17 (septet, J=6.8 Hz, 2H, CH), 2.45 (q, J=7.2 Hz, 4H, CH$_2$), 1.12 (d, J=6.8 Hz, 6H, CH(CH$_3$)$_2$), 1.07 (d, J=6.8 Hz, 6H, CH(CH$_3$)$_2$), 0.96 (t, J=7.2 Hz, 6H, CH$_2$CH$_3$) ppm. $^{13}$C{$^1$H} NMR (CDCl$_3$): δ 165.59, 149.63, 148.10, 147.27, 140.68, 137.22, 134.29, 134.26, 133.07, 131.95, 129.94, 127.96, 127.31, 126.99, 123.63, 116.12, 114.98, 111.83, 28.58, 24.78, 23.09, 14.95 ppm. Anal. Calc. (C$_{64}$H$_{74}$N$_4$): C, 85.48; H, 8.29; N, 6.23. Found: C, 85.71; H, 8.33; N, 6.26

Example 19

Synthesis of 1,2-phenylenebis-4-(N-(o-(2,6-diisopropylphenylamino) phenylmethylene)-2,6-diethylaniline) (compound (19))

1,2-phenylenebis-4-(N-(o-(2,6-diisopropylphenylamino) phenylmethylene)-2,6-diethylaniline) (compound (19)) was produced using the same manner as in Example 13, except that 2,6-diethylaniline was used in place of 2,6-diisopropylaniline.

Yield 95%. M.p. 246° C. IR (NaCl): 3190 (N—H), 1622 (C=N) cm$^{-1}$. $^1$H NMR (C$_6$D$_6$): δ 10.80 (s, 1H, N—H), 8.33 (s, 1H, H-4), 7.64 (AA'BB', 1H, H-2), 7.32 (AA'BB', 1H, H-1), 7.20-7.06 (m, 4H, H-9, H-10 and H-5), 7.12 (s, 2H, H-3), 6.97 (t, J=8.0 Hz, 1H, H-7), 6.59 (t, J=7.2 Hz, 1H, H-6), 6.41 (d, J=8.4 Hz, 1H, H-8), 3.19 (septet, J=7.2 Hz, 2H, CH), 2.72 (dq, J=14.4, 7.2 Hz, 2H, CH$_2$), 2.53 (dq, J=14, 7.6 Hz, 2H, CH$_2$), 1.16-1.08 (m, 18H, CH$_3$) ppm. $^{13}$C{$^1$H} NMR (C$_6$D$_6$): δ 166.23, 149.67, 147.43, 143.09, 142.26, 138.49, 138.00, 136.41, 134.89, 132.66, 130.40, 127.56, 127.42, 125.57, 117.04, 116.03, 112.29, 28.59, 25.87, 24.05, 15.68 ppm. Anal. Calc. (C$_{64}$H$_{74}$N$_4$): C, 85.48; H, 8.29; N, 6.23. Found: C, 85.31; H, 8.39; N, 6.25%.

Compounds (13) through (19) have the following formulae, respectively.

| Compound | 13 | 14 | 15 | 16 | 17 | 18 | 19 |
|---|---|---|---|---|---|---|---|
| R | iPr | Et | Me | Me | Et | Et | iPr |
| R' | iPr | Et | Me | iPr | Me | iPr | Et |

Example 20

Synthesis of 1,2-phenylenebis-4-(N-(o-(hydroketo)phenyl)-2,6-diethylaniline) (compound (20))

0.872 g (2.33 mmol) of compound (8) obtained in Example 8, 11 mg (0.050 mmol) of palladium diacetate, 0.628 g (6.53 mmol) of sodium t-butoxide, and 37.7 mg (0.070 mmol) of bis[2-(diphenylphosphino)phenyl]ether (DPEphos) were sequentially injected into a reaction flask. To the reaction flask, 1.34 g (5.83 mmol) of ethylene acetal compound of 2-bromobenzaldehyde which was obtained by reacting 2-bromobenzaldehyde with ethylene glycol according to a conventional method of protecting aldehyde, and 10 mL of toluene was added. The reaction mixture was stirred at 95° C. for 15 hours and 20 mL of distilled water and 50 mL of toluene were added to the resultant product. Then, a layer of toluene was separated and 444 mg of p-toluene sulfonic acid was added to the toluene layer and stirred. After 1 hour, 30 mL of a saturated aqueous solution of sodium bicarbonate was added and the toluene layer collected by layer separation was dried over anhydrous magnesium sulfate and distilled under reduced pressure to obtain an oily residue. The oily residue was purified by silica gel column chromatography using a mixed solvent of hexane:ethyl acetate=30:1 as an elution solution to obtain 1,2-phenylenebis-4-(N-(o-(hydroketo)phenyl)-2,6-diethylaniline) (compound (20)) (1.24 g).

Yield 87%. IR (KBr): 3286 (N—H), 1651 (C=O) cm$^{-1}$. $^1$H NMR (CDCl$_3$): δ 9.90 (s, 1H, N—H), 9.53 (s, 1H, C(O)H), 7.50 (d, J=7.6 Hz, 1H, H-5), 7.44 (AA'BB', 1H, H-10), 7.39 (AA'BB', 1H, H-11), 7.09 (t, J=7.2 Hz, 1H, H-7), 6.95 (s, 2H, H-9), 6.67 (t, J=7.6 Hz, 1H, H-6), 6.13 (d, J=8.4 Hz, 1H, H-8), 2.11 (s, 6H, CH$_3$) ppm. $^{13}$C{$^1$H} NMR (CDCl$_3$): δ 193.87 (carbonyl), 149.21, 139.90, 139.83, 136.05, 135.53, 134.41, 129.86, 127.26, 118.16, 115.70, 111.67, 18.17 ppm. HRMS calcd for C$_{36}$H$_{33}$O$_2$N$_2$, 525.2542 [M+H]$^+$; found, [M+H]$^+$; 525.2545 [M+H]$^+$.

Compound (20) has the following formula.

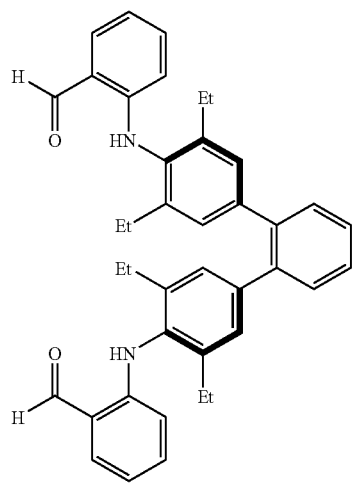

Example 21

Synthesis of 1,2-phenylenebis-4-(N-((o-(2,6-diethylphenyl)iminomethyl)phenyl)-2,6-diethylaniline) (compound (21))

0.337 g (1.8 mmol) of 2,6-diethylaniline was suspended in 20 mL of ethanol and then, 0.77 mL (9.33 mmol) of concentrated hydrochloric acid was added to the obtained suspension. After stirring for 1 hour, the color of the suspension was changed from yellow to white. The suspension was filtered off and washed with diethyl ether to obtain 0.29 g of 2,6-diethylaniline hydrochloride. The obtained compound was dissolved in 100 mL of anhydrous ethanol in a flask at 70° C., and a solution of 0.485 g (0.785 mmol) of compound (20) obtained in Example 20 in 50 mL of anhydrous ethanol was added to the flask. The resultant yellow solution was stirred at 70° C. for 3 days to obtain yellow precipitates. The reaction mixture was cooled to room temperature and 30 mL of a saturated aqueous solution of sodium bicarbonate was added, and then after stirring for 2 minutes, 150 mL of toluene was added to the resultant product. The toluene layer collected by layer separation was dried over anhydrous magnesium sulfate and distilled under reduced pressure to obtain a yellow residue. The residue was purified by silica gel column chromatography using toluene as an elution solution to obtain 1,2-phenylenebis-4-(N-((o-(2,6-diethylphenyl)iminomethyl)phenyl)-2,6-diethylaniline) (compound (21)) (0.606 g).

Yield 75%. M.p. 202° C. IR (KBr): 3178 (N—H), 1620 (C=N) cm$^1$. $^1$H NMR (CDCl$_3$): δ 10.55 (s, 1H, N—H), 8.31 (s, 1H, H-8), 7.50-7.25 (m, 2H, H-1 and H-2), 7.25-7.13 (m, 2H, H-9 and H-10), 7.27 (d, J=7.2 Hz, 1H, H-4), 7.19 (t, J=7.2 Hz, 1H, H-6), 6.91 (s, 2H, H-3), 6.68 (t, J=7.2 Hz, 1H, H-5), 6.37 (d, J=7.6 Hz, 1H, H-7), 2.58-2.27 (m, 8H, CH$_2$), 0.96 (t, J=6.8 Hz, 6H, CH$_3$), 0.94 (t, J=6.8 Hz, 6H, CH$_3$) ppm. Anal. Calc. (C$_{60}$H$_{66}$N$_4$): C, 85.47; H, 7.89; N, 6.64. Found: C, 85.59; H, 8.32; N, 6.63%. Anal. Calc. (C$_{60}$H$_{66}$N$_4$): C, 85.47; H, 7.89; N, 6.64. Found: C, 85.79; H, 8.22; N, 6.73%.

Compound (21) has the following formula.

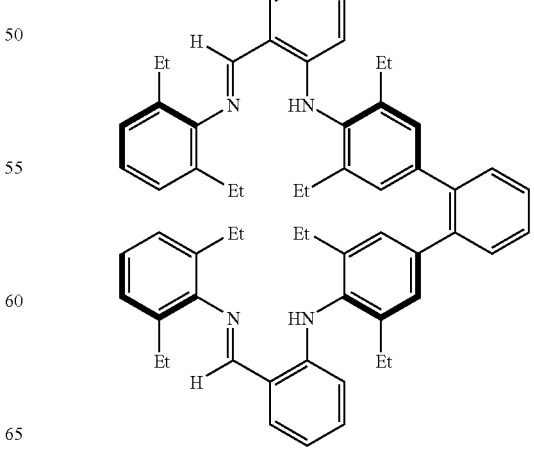

Example 22

Synthesis of 13•(bis(methylzinc)) compound (compound (22)) and 13•(bis(μ-methylsulfinato)zinc) compound (compound (23))

500 mg (0.526 mmol) of compound (13) obtained in Example 13 was dissolved in 7 mL of toluene and 2.63 mL (5.26 mmol) of a toluene solution containing 2.0 M dimethyl zinc was added to the resultant product. The mixture was stirred at room temperature for 2 days and the solvent was removed by distillation under reduced pressure to obtain a pure yellow solid (compound (22)), determined by $^1$H and $^{13}$C NMR spectrums.

$^1$H NMR ($C_6D_6$): δ 8.15 (s, 1H, H-4), 7.37 (AA'BB', 1H, H-2), 7.34-7.18 (m, 4H, H-9, H-10 and H-1), 7.14 (s, 2H, H-3), 7.10 (dd, J=8.0, 1.2 Hz, 1H, H-5), 6.90 (ddd, J=8.8, 6.8, 1.2 Hz, 1H, H-7), 6.54 (d, J=8.8 Hz, 1H, H-8), 6.36 (t, J=7.2 Hz, 1H, H-6), 3.37 (septet, J=6.8 Hz, 2H, CH), 3.14 (septet, J=6.8 Hz, 2H, CH), 1.29 (d, J=6.8 Hz, 6H, $CH_3$), 1.16 (d, J=6.8 Hz, 6H, $CH_3$), 1.15 (d, J=6.8 Hz, 6H, $CH_3$), 1.03 (d, J=6.8 Hz, 6H, $CH_3$), -0.51 (s, 3H, Zn—$CH_3$) ppm. $^{13}$C{$^1$H} NMR($C_6D_6$): δ 170.20, 158.34, 145.35, 144.30, 143.72, 141.38, 140.67, 140.51, 140.45, 137.92, 135.10, 130.79, 126.02, 125.79, 124.41, 116.96, 114.71, 113.92, 29.14 ($CH_3$), 28.65 ($CH_3$), 24.84 ($CH_3$), 24.33 (CH), 23.83 (CH), -16.40 (Zn—C) ppm.

The synthesized compound (22) was dissolved in 7 mL of toluene in a flask and the flask was coupled with a Schrenk line using glass and cooled to -10° C. When sulfur dioxide gas dried over phosphor pentaoxide in a 1.0 L flask was injected into the above flask through the Schrenk line, the solution becomes red, which was stirred at room temperature for 30 minutes. The solvent was removed under reduced pressure to obtain a yellow solid and the obtained solid was again dissolved in 3 mL of toluene. The solution was passed through diatomaceous earth to remove insoluble impurities. The yellow filtrate was treated with pentane to quantitatively obtain 13•(bis(μ-methylsulfinato)zinc) compound (compound (23)). According to $^1$H NMR and $^{13}$C NMR spectrums analyzed at room temperature, it was confirmed that three species are present in a ratio of 0.43:0.31:0.26. When these species were analyzed in toluene-$d_6$ at 100° C., they exhibited a broad peak together. In Example 22 and the following Examples, peaks originated from minor materials in $^{13}$C NMR data analyzed at room temperature were designated in italic style and peaks originated from the same carbon were designated in parentheses.

$^1$H NMR (toluene-$d_8$, 100° C.): δ 8.03 (s, 1H, H-4), 7.46-7.35 (br, 1H, H-2), 7.25 (AA'BB', 1H, H-1), 7.17-7.87 (m, 6H, H3, H-9, H-10, H-5), 6.78 (ddd, J=8.8, 6.8, 2.0 Hz, 1H, H-7), 6.30 (d, J=7.2 Hz, 1H, H-8), 6.19 (t, J=6.8 Hz, 1H, H-6), 3.48-3.30 (br, 2H, CH), 3.30-3.12 (br, 2H, CH), 1.98-1.70 (br, 1.5H, S—$CH_3$), 1.70-1.50 (br, 1.5H, S—$CH_3$), 1.24 (br d, J=6.8 Hz, 6H, $CH_3$), 1.04 (d, J=6.8 Hz, 6H, $CH_3$) ppm. $^{13}$C{$^1$H} NMR($C_6D_6$, 25° C.): δ (171.37, 171.29, 171.02), (160.35, 160.26, 160.04), 145.34, 145.19, 144.97, 144.85, 144.61, 144.51, 144.48, 144.40, 144.23, 143.95, 143.88, (140.74, 140.48, 139.94), (140.67, 140.43, 140.13), 138.45, 138.35, 138.24, 138.16, 137.97, 137.79, (134.17, 134.01, 133.96), 127.11, 127.05, 125.65, 125.32, 125.28, 125.14, 125.07, 124.70, 124.44, 124.40, 124.06, 123.96, (118.79, 118.60, 118.54), (114.19, 114.03, 113.55), (112.99, 112.98, 112.89), (48.01, 46.86, 46.06) (S—C), (28.65, 28.57, 28.40, 28.33, 28.26, 28.15) ($CH_3$), (26.66, 26.50, 26.37, 26.03, 25.88) ($CH_3$), (24.61, 24.44, 23.74, 22.99) (CH) ppm. Anal. Calc. ($C_{70}H_{86}N_4O_4S_2Zn_2$): C, 67.67; H, 6.98; N, 4.51. Found: C, 67.52; H, 6.75; N, 4.54%.

Example 23

14•(bis(methylzinc)) compound (compound (24)) and 14•(bis(μ-methylsulfinato)zinc) compound (compound (25))

14•(bis(methylzinc)) compound (compound (24)) was quantitatively synthesized using the same manner as in Example 22, except that compound (14) obtained in Example 14 was used in place of compound (13) and the length of time of stirring with dimethyl zinc complex was changed from 2 days to 1 day.

$^1$H NMR ($C_6D_6$): δ 7.99 (s, 1H, H-4), 7.50 (AA'BB', 1H, H-2), 7.29 (AA'BB', 1H, H-1), 7.22-7.10 (A2B, 3H, H-9 and H-10), 7.06 (s, 2H, H-3), 7.01 (dd, J=7.6, 1.6 Hz, 1H, H-5), 6.91 (ddd, J=8.4, 7.0, 1.2 Hz, 1H, H-7), 6.52 (d, J=8.8 Hz, 1H, H-8), 6.38 (t, J=8.0 Hz, 1H, H-6), 2.70 (dq, J=14.8, 7.2 Hz, 2H, $CH_2$), 2.54 (dq, J=14.8, 7.2 Hz, 2H, $CH_2$), 2.52 (dq, J=14.8, 7.2 Hz, 2H, $CH_2$), 2.45 (dq, J=14.8, 7.2 Hz, 2H, $CH_2$), 1.15 (t, J=7.2 Hz, 6H, $CH_3$), 1.02 (t, J=7.2 Hz, 6H, $CH_3$), -0.56 (s, 3H, Zn—$CH_3$) ppm. $^{13}$C{$^1$H} NMR ($CDCl_3$): δ 170.27, 157.81, 146.82, 146.23, 140.96, 140.01, 139.05, 137.96, 135.90, 135.17, 130.81, 128.74, 127.83, 127.43, 125.39, 116.35, 114.77, 113.73, 25.59 ($CH_2$), 25.41 ($CH_2$), 15.55 ($CH_3$), 15.19 ($CH_3$), -16.78 (Zn—C) ppm.

14•(bis(μ-methylsulfinato)zinc) compound (compound (25)) was synthesized from compound (24) using the same manner as in Example 22. According to $^1$H NMR and $^{13}$C NMR spectrums analyzed at room temperature, it was confirmed that three isomers are present in a ratio of 0.67:0.26:0.07.

$^1$H NMR (toluene-$d_8$, 100° C.): δ 7.81 (s, 1H, H-4), 7.41 (AA'BB', 1H, H-2), 7.27 (AA'BB', 1H, H-1), 7.10-6.90 (A2B, 3H, H-9 and H-10), 6.87 (s, 2H, H-3), 6.82 (d, J=8.4, 1H, H-5), 6.77 (ddd, J=8.4, 7.0, 1.2 Hz, 1H, H-7), 6.25 (d, J=8.8 Hz, 1H, H-8), 6.19 (t, J=8.0 Hz, 1H, H-6), 2.78-2.44 (m, 8H, $CH_2$), 1.81-1.55 (br, 3H, S—$CH_3$), 1.12 (t, J=7.2 Hz, 6H, $CH_3$), 1.10 (t, J=7.2 Hz, 6H, $CH_3$) ppm. $^{13}$C{$^1$H} NMR($C_6D_6$, 25° C.): δ (171.80, 171.59), (159.60, 159.46), (146.35, 146.23), (145.91, 145.77), 143.56, 140.12, 139.88, 138.48, 135.55, 135.21, 134.85, 134.67, 128.80, 128.64, 127.29, 127.10, 126.39, 126.26, 126.01, 125.65, 125.01, 124.74, (117.00, 116.77), (114.10, 113.68), 112.63, (48.06, 47.18, 47.04, 46.42) (S—C), (24.84, 24.65, 24.27, 23.99) ($CH_2$), (15.32, 15.23, 14.60, 14.50) ($CH_3$) ppm. Anal. Calc. ($C_{62}H_{70}N_4O_4S_2Zn_2$): C, 65.89; H, 6.24; N, 4.96. Found: C, 65.60; H, 6.31; N, 4.98%.

Example 24

Synthesis of 15•(bis(methylzinc)) compound (compound (26)) and 15•(bis(μ-methylsulfinato)zinc) compound (compound (27))

15•(bis(methylzinc)) compound (compound (26)) was quantitatively synthesized using the same manner as in Example 22, except that compound (15) obtained in Example 15 was used in place of compound (13) and the length of time of stirring with dimethyl zinc complex was changed from 2 days to 1 day.

$^1$H NMR ($C_6D_6$): δ 7.77 (s, 1H, H-4), 7.47 (AA'BB', 1H, H-2), 7.29 (AA'BB', 1H, H-1), 7.18-7.02 (A2B, 3H, H-9 and H-10), 7.02 (s, 2H, H-3), 6.93 (dd, J=8.0, 2.0 Hz, 1H, H-5), 6.90 (ddd, J=8.6, 6.4, 2.0 Hz, 1H, H-7), 6.48 (d, J=8.8 Hz, 1H, H-8), 6.38 (t, J=8.0 Hz, 1H, H-6), 2.18 (s, 6H, CH$_3$), 2.01 (s, 6H, CH$_3$), −0.58 (s, 3H, Zn—CH$_3$) ppm. $^{13}$C{$^1$H} NMR(C$_6$D$_6$): δ 169.70, 156.73, 147.46, 147.38, 140.45, 139.41, 137.84, 135.03, 133.02, 130.68, 130.28, 129.57, 129.01, 127.70, 124.58, 115.35, 114.88, 113.53, 18.79 (CH$_3$), 18.57 (CH$_3$), −17.57 (Zn—C) ppm.

15•(bis(μ-methylsulfinato)zinc) compound (compound (27)) was synthesized from compound (26) using the same manner as in Example 22. According to $^1$H NMR and $^{13}$C NMR spectrums analyzed at room temperature, it was confirmed that only a single isomer is present.

$^1$H NMR (C$_6$D$_6$, 25° C.): δ 7.61 (s, 1H, H-4), 7.49 (AA'BB', 1H, H-2), 7.32 (AA'BB', 1H, H-1), 7.18-6.82 (A2B, 3H, H-9 and H-10), 6.85 (d, J=8.0, 1H, H-5), 6.83-6.76 (m, 3H, H-3 and H-7), 6.34 (d, J=8.8 Hz, 1H, H-8), 6.30 (t, J=7.2 Hz, 1H, H-6), 2.25 (s, 6H, CH$_3$), 2.11 (s, 6H, CH$_3$), 1.53 (s, 3H, S—CH$_3$) ppm. $^{13}$C{$^1$H} NMR(C$_6$D$_6$, 25° C.): δ 171.48; 158.32, 147.31, 146.95, 142.79, 139.36, 138.60, 135.20, 134.54, 130.40, 129.30, 129.02, 127.12, 125.65, 124.62, 115.56, 113.88, 112.64, 43.59 (S—C), 18.77 (CH$_3$), 18.50 (CH$_3$) ppm. Anal. Calc. (C$_{54}$H$_{54}$N$_4$O$_4$S$_2$Zn$_2$): C, 63.71; H, 5.35; N, 5.50. Found: C, 63.50; H, 5.32; N, 5.41%.

Example 25

Synthesis of 16•(bis(methylzinc)) compound (compound (28)) and 16•(bis(μ-methylsulfinato)zinc) compound (compound (29))

16•(bis(methylzinc)) compound (compound (28)) was quantitatively synthesized using the same manner as in Example 22, except that compound (16) obtained in Example 16 was used in place of compound (13) and the length of time of stirring with dimethyl zinc complex was changed from 2 days to 1 day.

$^1$H NMR (C$_6$D$_6$): δ 7.74 (s, 1H, H-4), 7.49 (AA'BB', 1H, H-2), 7.30 (AA'BB', 1H, H-1), 7.28-7.00 (A2B, 3H, H-9 and H-10), 7.03 (s, 2H, H-3), 6.93 (dd, J=7.6, 1.6 Hz, 1H, H-5), 6.91 (ddd, J=8.4, 6.8, 1.2 Hz, 1H, H-7), 6.53 (d, J=8.8 Hz, 1H, H-8), 6.39 (t, J=7.6 Hz, 1H, H-6), 3.31 (septet, J=6.8 Hz, 2H, CH), 2.04 (s, 6H, CH$_3$), 1.24 (d, J=6.8 Hz, 6H, CH$_3$), 1.13 (d, J=6.8 Hz, 6H, CH$_3$), −0.58 (s, 3H, Zn—CH$_3$) ppm. $^{13}$C{$^1$H} NMR(C$_6$D$_6$): δ 169.82, 158.28, 147.62, 144.48, 143.74, 140.69, 139.57, 138.00, 134.87, 130.84, 130.45, 129.79, 125.97, 124.38, 116.86, 114.97, 113.58, 28.56 (CH), 24.93 (CH(CH$_3$)$_2$), 24.18 (CH(CH$_3$)$_2$), 19.00 (CH$_3$), −16.98 (Zn—C) ppm.

16•(bis(μ-methylsulfinato)zinc) compound (compound (29)) was synthesized from compound (28) using the same manner as in Example 22. According to $^1$H NMR and $^{13}$C NMR spectrums analyzed at room temperature, it was confirmed that isomers of primary product are present in an amount of 90% or more.

$^1$H NMR (toluene-d$_8$, 100° C.). $^1$H NMR (toluene-d$_8$, 100° C.): $^1$H NMR (C$_6$D$_6$): δ 7.69 (s, 1H, H-4), 7.35 (AA'BB', 1H, H-2), 7.24 (AA'BB', 1H, H-1), 7.25-6.90 (A2B, 3H, H-9 and H-10), 6.83-6.69 (m, 4H, H-3, H-5 and H-7), 6.28 (d, J=8.8 Hz, 1H, H-8), 6.19 (t, J=6.8 Hz, 1H, H-6), 3.36 (br, 2H, CH), 2.12 (s, 6H, CH$_3$), 1.60-1.40 (br, 3H, S—CH$_3$), 1.23 (br d, J=6.8 Hz, 6H, CH$_3$), 1.02 (d, J=6.8 Hz, 6H, CH$_3$) ppm. $^{13}$C{$^1$H} NMR(C$_6$D$_6$, 25° C.): δ 171.49, 159.91, 146.83, 144.86, 144.56, 142.96, 139.54, 138.50, 134.25, 130.11, 129.40, 128.83, 127.07, 125.64, 124.48, 118.26, 113.89, 112.52, 46.67 (S—C), 28.13 (CH(CH$_3$)$_2$), 26.03 (CH(CH$_3$)$_2$), 24.42 (CH), 18.75 (CH$_3$). Data of peaks originated from isomers of side product were not designated.

Anal. Calc. (C$_{62}$H$_{70}$N$_4$O$_4$S$_2$Zn$_2$y: C, 65.89; H, 6.24; N, 4.96. Found: C, 66.01; H, 6.18; N, 4.93%.

Example 26

Synthesis of 17•(bis(methylzinc)) compound (compound (30)) and 17•(bis(μ-methylsulfinato)zinc) compound (compound (31))

17•(bis(methylzinc)) compound (compound (30)) was quantitatively synthesized using the same manner as in Example 22, except that compound (17) obtained in Example 17 was used in place of compound (13) and the length of time of stirring with dimethyl zinc complex was changed from 2 days to 1 day.

$^1$H NMR (C$_6$D$_6$): δ 7.99 (s, 1H, H-4), 7.50 (AA'BB', 1H, H-2), 7.29 (AA'BB', 1H, H-1), 7.20-7.04 (A2B, 3H, H-9 and H-10), 7.07 (s, 2H, H-3), 7.02 (dd, J=8.0, 1.6 Hz, 1H, H-5), 6.90 (ddd, J=8.4, 7.2, 2.0 Hz, 1H, H-7), 6.51 (d, J=9.2 Hz, 1H, H-8), 6.39 (t, J=7.2 Hz, 1H, H-6), 2.51 (dq, J=14.4, 7.2 Hz, 2H, CH$_2$), 2.43 (dq, J=14.4, 7.2 Hz, 2H, CH$_2$), 2.22 (s, 6H, CH$_3$), 1.01 (t, J=7.2 Hz, 6H, CH$_3$), −0.55 (s, 3H, Zn—CH$_3$) ppm. $^{13}$C{$^1$H} NMR (C$_6$D$_6$): δ 170.20, 156.99, 147.48, 146.84, 140.89, 140.00, 138.00, 135.86, 135.36, 133.23, 130.86, 129.23, 128.75, 127.83, 124.81, 115.61, 114.93, 113.85, 25.59 (CH$_2$), 18.79 (CH$_3$), 15.19 (CH$_3$), −17.20 (Zn—C) ppm.

17•(bis(μ-methylsulfinato)zinc) compound (compound (31)) was synthesized from compound (30) using the same manner as in Example 22. According to $^1$H NMR and $^{13}$C NMR spectrums analyzed at room temperature, it was confirmed that isomers of primary product are present in an amount of 90% or more.

$^1$H NMR (toluene-d$_8$, 100° C.): δ 7.82 (s, 1H, H-4), 7.41 (AA'BB', 1H, H-2), 7.27 (AA'BB', 1H, H-1), 7.10-6.90 (A2B, 3H, H-9 and H-10), 6.88 (s, 2H, H-3), 6.83 (d, J=7.6 Hz, 1H, H-5), 6.77 (t, J=6.8 Hz, 1H, H-7), 6.22 (d, J=8.8 Hz, 1H, H-8), 6.19 (t, J=7.2 Hz, 1H, H-6), 2.60 (q, J=7.2 Hz, 2H, CH$_2$), 2.62-2.50 (br, 2H, CH$_2$), 2.15 (s, 6H, CH$_3$), 1.82-1.60 (br, 3H, S—CH$_3$), 1.11 (t, J=7.2 Hz, 6H, CH$_3$) ppm. $^{13}$C{$^1$H} NMR (C$_6$D$_6$, 25° C.): δ 171.95, 158.47, 147.30, 146.06, 143.51, 140.11, 138.57, 135.19, 134.61, 128.96, 128.80, 128.51, 128.24, 127.11, 124.63, 115.66, 113.61, 112.70, 46.98 (S—C), 24.87 (CH$_2$), 18.56 (CH$_3$), 15.26 (CH$_3$) ppm. Data of peaks originated from isomers of side product were not designated. Anal. Calc. (C$_{58}$H$_{62}$N$_4$O$_4$S$_2$Zn$_2$): C, 64.86; H, 5.82; N, 5.22. Found: C, 65.05; H, 5.77; N, 5.20%.

Example 27

Synthesis of 18•(bis(methylzinc)) compound (compound (32)) and 18•(bis(μ-methylsulfinato)zinc) compound (compound (33))

18•(bis(methylzinc)) compound (compound (32)) was quantitatively synthesized using the same manner as in Example 22, except that compound (18) obtained in Example 18 was used in place of compound (13) and the length of time of stirring with dimethyl zinc complex was changed from 2 days to 1 day.

$^1$H NMR (C$_6$D$_6$): δ 7.96 (s, 1H, H-4), 7.51 (AA'BB', 1H, H-2), 7.30 (AA'BB', 1H, H-1), 7.28-7.18 (A2B, 3H, H-9 and H-10), 7.06 (s, 2H, H-3), 7.00 (dd, J=7.6, 1.2 Hz, 1H, H-5), 6.90 (ddd, J=8.4, 7.2, 1.6 Hz, 1H, H-7), 6.53 (d, J=8.8 Hz, 1H, H-8), 6.38 (t, J=7.2 Hz, 1H, H-6), 3.34 (septet, J=6.8 Hz, 2H, CH), 2.53 (dq, J=14.4, 7.2 Hz, 2H, CH$_2$), 2.44 (dq, J=14.4, 7.2 Hz, 2H, CH$_2$), 1.27 (d, J=6.8 Hz, 6H, CH(CH$_3$)$_2$), 1.14 (d, J=6.8 Hz, 6H, CH(CH$_3$)$_2$), 1.03 (t, J=7.2 Hz, 6H, CH$_2$CH$_3$), −0.56 (s, 3H, Zn—CH$_3$) ppm. $^{13}$C{$^1$H} NMR (C$_6$D$_6$): δ 170.21, 158.33, 146.81, 144.38, 143.74, 140.99, 140.01, 137.98, 135.86, 134.99, 130.81, 128.70, 127.82, 125.99, 124.41, 116.92, 114.80, 113.70, 28.59, 25.56, 24.87, 24.27, 15.14 (CH$_2$CH$_3$), −16.59 (Zn—C) ppm.

18•(bis(μ-methylsulfinato)zinc) compound (compound (33)) was synthesized from compound (32) using the same manner as in Example 22. According to $^1$H NMR and $^{13}$C NMR spectrums analyzed at room temperature, it was confirmed that isomers of primary product are present in an amount of 90% or more.

$^1$H NMR (toluene-d$_8$, 100° C.): $^1$H NMR (toluene-d$_8$, 100° C.): δ 7.80 (s, 1H, H-4), 7.40 (AA'BB', 1H, H-2), 7.26 (AA'BB', 1H, H-1), 7.15-6.90 (A2B, 3H, H-9 and H-10), 6.87 (s, 2H, H-3), 6.81 (d, J=7.6 Hz, 1H, H-5), 6.77 (ddd, J=8.4, 7.2, 1.6 Hz, 1H, H-7), 6.29 (d, J=8.8 Hz, 1H, H-8), 6.19 (t, J=7.6 Hz, 1H, H-6), 3.50-3.26 (br, J=6.8 Hz, 2H, CH), 2.76-2.40 (br, 4H, CH$_2$), 1.92-1.48 (br, 3H, S—CH$_3$), 1.32-1.18 (br, 6H, CH(CH$_3$)$_2$), 1.10 (t, J=7.2 Hz, 6H, CH$_2$CH$_3$), 1.04 (d, J=6.8 Hz, 6H, CH(CH$_3$)$_2$) ppm. $^{13}$C{$^1$H} NMR (C$_6$D$_6$, 25° C.): δ 171.77, 159.95, 145.94, 144.91, 144.57, 143.66, 140.13, 138.44, 135.19, 134.26, 128.68, 127.65, 127.10, 125.66, 124.44, 118.35, 113.76, 112.63, 46.97 (S—C), 28.17, 26.06, 24.78, 24.52, 15.20 (CH$_2$CH$_3$) ppm. Data of peaks originated from isomers of side product were not designated. Anal. Calc. (C$_{66}$H$_{78}$N$_4$O$_4$S$_2$Zn$_2$): C, 66.82; H, 6.63; N, 4.72. Found: C, 67.12; H, 6.68; N, 4.70%.

Figure 2:
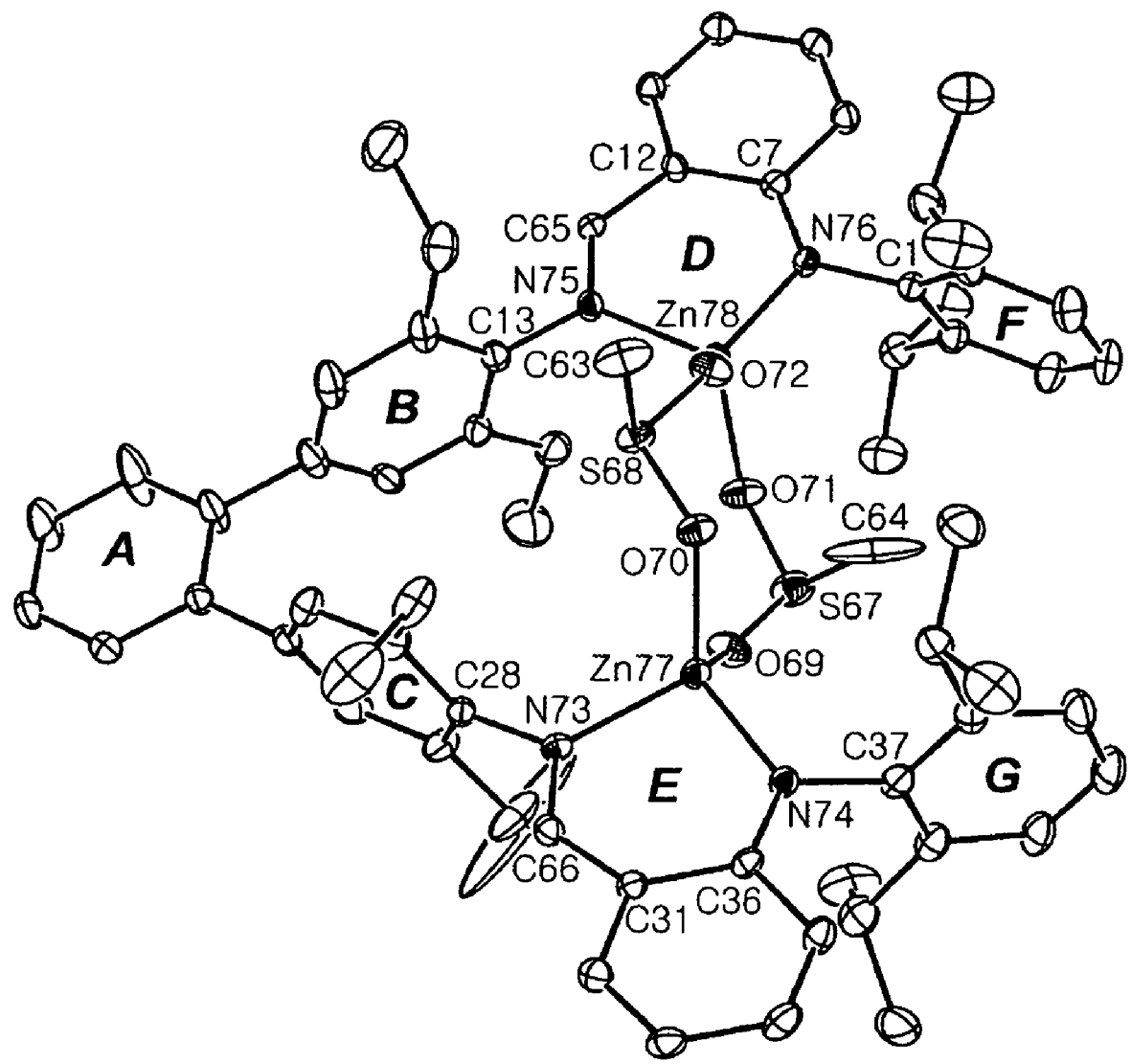
FIG. 2 is an X-ray diffraction diagram of a single crystal of compound (33) according to an embodiment of the present invention.

An X-ray diffraction structure of a single crystal of compound (33) produced in Example 27 was found. The chemical structure of compound (33) is shown in FIG. 2.

Example 28

Synthesis of 19•(bis(methylzinc)) compound ((compound (34)) and 19•(bis(μ-methylsulfinato)zinc) compound (compound (35))

19•(bis(methylzinc)) compound (compound (34)) was quantitatively synthesized using the same manner as in Example 22, except that compound (19) obtained in Example 19 was used in place of compound (13) and the length of time of stirring with dimethyl zinc complex was changed from 2 days to 1 day.

$^1$H NMR (C$_6$D$_6$): δ 8.16 (s, 1H, H-4), 7.47 (AA'BB', 1H, H-2), 7.26 (AA'BB', 1H, H-1), 7.23-7.08 (A2B, 3H, H-9 and H-10), 7.14 (s, 2H, H-3), 7.01 (d, J=7.2 Hz, 1H, H-5), 6.90 (t, J=7.2 Hz, 1H, H-7), 6.54 (d, J=9.2 Hz, 1H, H-8), 6.37 (t, J=6.8 Hz, 1H, H-6), 3.14 (septet, J=6.8 Hz, 2H, CH), 2.74 (dq, J=14.4, 7.2 Hz, 2H, CH$_2$), 2.57 (dq, J=14.4, 7.2 Hz, 2H, CH$_2$), 1.18 (t, J=7.2 Hz, 6H, CH$_2$CH$_3$), 1.15 (d, J=6.8 Hz, 6H, CH(CH$_3$)$_3$), 1.04 (d, J=6.8 Hz, 6H, CH(CH$_3$)$_3$), −0.49 (s, 3H, Zn—CH$_3$) ppm. $^{13}$C{$^1$H} NMR (C$_6$D$_6$): δ 170.27, 157.84, 146.17, 145.40, 141.38, 140.73, 140.46, 139.05, 137.92, 135.31, 130.81, 127.84, 127.47, 125.82, 125.45, 116.41, 114.73, 113.95, 29.13, 25.43, 24.38, 23.83, 15.56 (CH$_2$CH$_3$), −16.61 (Zn—C) ppm.

19•(bis(μ-methylsulfinato)zinc) compound (compound (35)) was synthesized from compound (34) using the same manner as in Example 22. According to $^1$H NMR and $^{13}$C NMR spectrums analyzed at room temperature, it was confirmed that three isomers are present in a ratio of 0.41:0.40:0.19.

$^1$H NMR (toluene-d$_8$, 100° C.): δ 8.04 (s, 1H, H-4), 7.40 (AA'BB', 1H, H-2), 7.25 (AA'BB', 1H, H-1), 7.12-6.89 (m, 6H, H-3, H-5, H-9 and H-10), 6.78 (ddd, J=8.8, 6.8, 2.0 Hz, 1H, H-7), 6.26 (d, J=8.4 Hz, 1H, H-8), 6.20 (t, J=8.0 Hz, 1H, H-6), 3.24 (septet, J=6.8 Hz, 2H CH), 2.76-2.52 (m, 4H, CH$_2$), 2.00-1.50 (br, 3H, S—CH$_3$), 1.25 (d, J=6.8 Hz, 6H, CH(CH$_3$)$_3$), 1.09 (t, J=7.2 Hz, 6H, CH$_2$CH$_3$), 1.06 (d, J=6.8 Hz, 6H, CH(CH$_3$)$_3$) ppm. $^{13}$C{$^1$H} NMR(C$_6$D$_6$, 25° C.): δ (171.49, 171.34, 170.81), 159.57, (146.71, 146.47, 146.35), 144.42, 144.28, 143.93, 143.90, 143.83, 143.08, 140.81, 140.54, 140.45, 140.32, 140.25, 140.0, 139.51, 139.45, 138.41, (134.82, 134.65, 134.61), 129.53, 129.40, 129.27, 128.52, 127.10, 126.38, 126.23, 125.94, 125.65, 125.25, 125.00, 124.88, 124.83, 124.75, 124.63, 116.98, (114.14, 113.94, 113.52), 112.89, 112.81, (47.61, 47.18, 46.97, 46.24) (S—C), 28.70, 28.60, 28.18, 26.75 26.33, 26.26, 26.19, 24.37, 24.18, 24.11, 24.10, 23.98, 23.94, 23.73, 23.08, 22.97, (14.63, 14.57, 14.52) (CH$_2$CH$_3$) ppm. Anal. Calc. (C$_{66}$H$_{78}$N$_4$O$_4$S$_2$Zn$_2$): C, 66.82; H, 6.63; N, 4.72. Found: C, 66.98; H, 6.71; N, 4.75%.

Compounds (23), (25), (27), (29), (31), (33) and (35) have the following formulae, respectively.

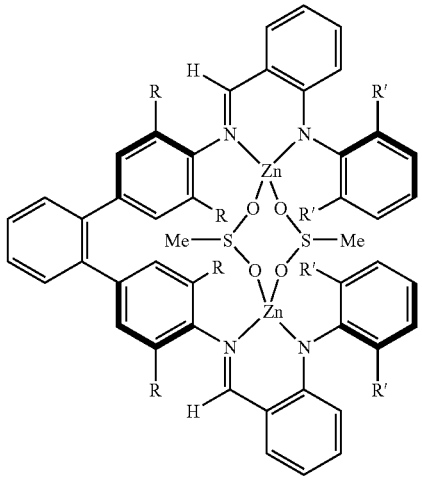

| Compound | 23 | 25 | 27 | 29 | 31 | 33 | 35 |
|---|---|---|---|---|---|---|---|
| R | iPr | Et | Me | Me | Et | Et | iPr |
| R' | iPr | Et | Me | iPr | Me | iPr | Et |

Example 29

Synthesis of 20•(bis(methylzinc)) compound (compound (36)) and 20•(bis(μ-methylsulfinato)zinc) compound (compound (37))

20•(bis(methylzinc)) compound (compound (36)) was quantitatively synthesized using the same manner as in Example 22, except that compound (21) obtained in Example 21 was used in place of compound (13) and the length of time of stirring with dimethyl zinc complex was changed from 2 days to 3 days.

$^1$H NMR (C$_6$D$_6$): δ 8.56 (s, 1H, H-4), 7.67 (AA'BB', 1H, H-2), 7.44 (AA'BB', 1H, H-1), 7.00 (s, 2H, H-9), 6.99 (dd, J=8.0, 1.6 Hz, 1H, H-5), 6.92 (ddd, J=8.8, 7.6, 2.0 Hz, 1H, H-7), 6.64 (d, J=8.4 Hz, 1H, H-8), 6.40 (ddd, J=8.0, 6.8, 1.2 Hz, 1H, H-6), 2.65-2.50 (br, 4H, CH$_2$), 2.45-2.29 (br, 4H, CH$_2$), 1.20-1.03 (br, 6H, CH$_3$), 1.00-0.80 (br, 6H, CH$_3$), −1.03 (s, 3H, Zn—CH$_3$) ppm. $^{13}$C{$^1$H} NMR(C$_6$D$_6$): δ 170.84, 157.02, 145.05, 143.32, 141.46, 140.42, 136.96, 134.69, 130.28, 127.44, 125.78, 119.14, 115.43, 113.42, 25.44, 25.40, 15.06, 14.97, −15.14 (Zn—CH$_3$) ppm.

(bis(μ-methylsulfinato)zinc) compound (compound (37)) was synthesized from compound (36) using the same manner as in Example 22. According to $^1$H NMR and $^{13}$C NMR spectrums analyzed at room temperature, it was confirmed that two isomers are present in a ratio of 0.77:0.23.

$^1$H NMR (toluene-d$_8$, 100° C.): δ 7.76 (s, 1H, H-4), 7.57 (AA'BB', 1H, H-2), 7.34 (AA'BB', 1H, H-1), 7.01 (s, 2H, H-9), 6.89 (dd, J=8.0, 1.6 Hz, 1H, H-5), 6.82 (ddd, J=8.8, 7.6, 2.0 Hz, 1H, H-7), 6.60 (d, J=8.4 Hz, 1H, H-8), 6.39 (t, J=8.0 Hz, 1H, H-6), 2.55-2.41 (m, 8H, CH$_2$), 1.55-1.25 (br, 3H, S—CH$_3$), 1.11 (t, J=7.2 Hz, 6H, CH$_3$), 1.08 (t, J=7.2 Hz, 6H, CH$_3$) ppm. $^{13}$C{$^1$H} NMR(C$_6$D$_6$): δ (171.49, 171.34), 159.57, (146.71, 146.47), 144.42, 143.93, 143.83, 140.81, 140.45, 140.0, 139.51, 139.45, (134.82, 134.65), 129.53, 129.27, 128.33, 127.10, 126.67, 126.38, 125.94, 125.65, 125.25, 125.00, 124.88, 124.75, 124.63, 116.98, (113.94, 113.52), 112.89, 112.81, (47.61, 47.18, 46.24) (S—C), 24.36, 24.28, 14.67, 14.50 ppm. Anal. Calc. (C$_{36}$H$_{32}$N$_2$O$_6$S$_2$Zn$_2$): C, 55.18; H, 4.12; N, 3.58. Found: C, 55.23; H, 4.32; N, 3.54%.

Compound (37) has the following formula.

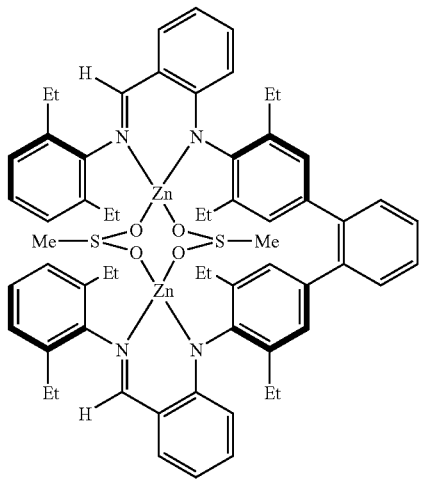

Examples 30-39

Copolymerization of Cyclohexene Oxide and Carbon Dioxide

A bimetallic zinc catalyst (14.1 μmol) according to an embodiment of the present invention was placed into a 50 mL high pressure reactor within a glovebox, and then 8.0 mL (79 mmol) of cyclohexene oxide was added to dissolve the catalyst. The reactor was sealed and removed from the glovebox. The amount of cyclohexene oxide was twice (16.0 mL) in Example 35 and three times (24.0 mL) in Example 36. The reactor was immersed in a constant temperature bath at 80° C. and the pressure of carbon dioxide in the reactor was set to 12 atm. Polymerization was performed for 5, 10, or 15 hours, as described in Table 1 and the carbon dioxide was discharged from the reactor. Cyclohexene oxide remained in the mixture was discharged by vaporizing under reduced pressure. The residue was dissolved in 10 mL of methylene chloride and treated with 50 mL of methanol to obtain polymer powders. The results of copolymerization are shown in Table 1.

Comparative Example 1

Copolymerization of Cyclohexene Oxide and Carbon Dioxide Using a Comparative Catalyst Copolymerization was performed in the conditions described in Table 1 using the same manner as in Example 31. A zinc compound, {[(C$_6$H$_3$Et$_2$)N═C(Me)CH═C(Me)N(C$_6$H$_3$Et$_2$)$_K$$^2$-N,N]Zn(μ-OS(O)Et)}$_2$ was used as a comparative catalyst.

The results of polymerization are shown in Table 1.

It was confirmed from the results that the bimetallic zinc complex according to an embodiment of the present invention has a higher activity and produces a higher molecular weight polymer having a higher carbonate content at [CHO]/[Zn]=5600 than a zinc catalyst containing unbridged diketiminate ligands.

TABLE 1

| Example | Catalyst | Time (hr) | TON[b] | TOF[c] | Carbonate content (%)[d] | M$_n$[e] | M$_w$/M$_n$[e] |
|---|---|---|---|---|---|---|---|
| 30 | 23 | 10 | 250 | 25 | 88 | 45000 | 2.1 |
| 31 | 25 | 10 | 1680 | 168 | 96 | 129000 | 1.3 |
| 32 | 27 | 10 | 1060 | 106 | 93 | 80000 | 1.3 |
| 33 | 29 | 5 | 1560 | 312 | 94 | 225000 | 1.7 |
| 34[f] | 29 | 10 | 2720 | 272 | 91 | 261000 | 1.6 |
| 35[g] | 29 | 15 | 2980 | 200 | 91 | 284000 | 1.7 |
| 36 | 31 | 10 | 670 | 67 | 93 | 77000 | 1.3 |
| 37 | 33 | 5 | 1450 | 308 | 93 | 205000 | 1.6 |
| 38 | 35 | 10 | 670 | 67 | 85 | 88000 | 1.3 |
| 39 | 37 | 10 | 1700 | 170 | 90 | 115000 | 1.7 |
| Comparative Example 1 | BDI[h] | 10 | 56 | 5.6 | 74 | 27000 | 1.8 |

[a]Conditions of polymerization: cyclohexene oxide (CHO) 8.0 mL, [CHO]/[Zn] = 5600, 80° C., carbon dioxide 12 atm.
[b]TON = turnover number, i.e., the amount of CHO consumed per mol of zinc.
[c]TOF = turnover frequency, i.e., the amount of CHO consumed per hour per mol of zinc.
[d]$^1$H NMR analytical results.
[e]GPC analytical results (elution solution: tetrahydrofuran).
[f]cyclohexene oxide (CHO) 16 mL, [CHO]/[Zn] = 11200.
[g]cyclohexene oxide (CHO) 24 mL, [CHO]/[Zn] = 16800.
[h]BDI = {[(C$_6$H$_3$Et$_2$)N═C(Me)CH═C(Me)N(C$_6$H$_3$Et$_2$)]Zn(μ-OS(O)Et)}$_2$.

Example 41

Copolymerization of 2,3-epoxynorbornene and carbon dioxide

Copolymerization of 2,3-epoxynorbornene and carbon dioxide was performed using the same method as in Example 34 (using Compound 29 as catalyst), except that 5 g of 2,3-epoxynorbornene was used in place of cyclohexene oxide and 5 mL of toluene was used as a solvent for polymerization. TON=750.

Example 42

Copolymerization of Propylene Oxide and Carbon Dioxide

Copolymerization of propylene oxide and carbon dioxide was performed using the same method as in Example 34 (using Compound 29 as catalyst), except that 10 g of propylene oxide was used in place of cyclohexene oxide and 5 mL of toluene was used as a solvent for polymerization. TON=3400.

A bimetallic zinc complex according to the present invention has a distance between zinc-zinc atoms which is maintained in a limited range regardless of its concentration in a reaction medium for polymerization of an epoxy compound and carbon dioxide. Thus, the bimetallic zinc complex can have a polymerization activity even at a high ratio of monomer/catalyst, thereby reducing a catalyst amount to be used, which is economically advantageous. Further, the bimetallic zinc complex can produce a high molecular weight polycarbonate.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A bimetallic zinc complex having formula 1:

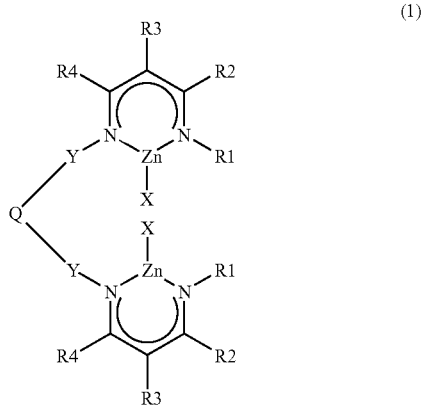

(1)

wherein
each of N~N chelate ligands is a monovalent anion and together with zinc forms a 6-membered ring,
R1 is a $C_1$-$C_{20}$ alkyl radical having at least one hydrogen atom unsubstituted or substituted by a halogen atom or a $C_6$-$C_{20}$ aryl radical having at least one hydrogen atom unsubstituted or substituted by a halogen atom, and the R1 radicals are either identical or different from each other,
R2 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R2 radicals are either identical or different from each other,
R3 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R3 radicals are either identical or different from each other,
R4 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R4 radicals are either identical or different from each other,
either R2 and R3, or R3 and R4 may be linked to each other to form a ring,
X is a monovalent anion selected from a $C_1$-$C_{20}$ alkoxy radical having at least one hydrogen atom unsubstituted or substituted by a halogen atom, carboxy, alkylsulfinato, and amido, and the X monovalent anions are either identical or different from each other and each X may be coordinated to only a metallic zinc atom or form a bridged structure between two metallic zinc atoms,
Y is a carbon diradical and may have at least one hydrogen substituted by halogen, and the Y diradicals are either identical or different from each other, and
Q is a $C_1$-$C_{20}$ alkyl diradical having at least one hydrogen atom unsubstituted or substituted by a halogen atom or a $C_6$-$C_{20}$ aryl diradical having at least one hydrogen atom unsubstituted or substituted by a halogen atom.

2. The bimetallic zinc complex of claim 1 having formula 2:

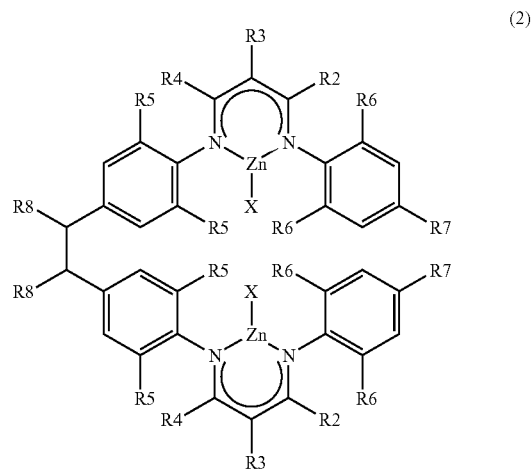

(2)

wherein
each of N~N chelate ligands is a monovalent anion and together with zinc forms a 6-membered ring,
R2 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R2 radicals are either identical or different from each other,
R3 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R3 radicals are either identical or different from each other,
R4 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R4 radicals are either identical or different from each other,
either R2 and R3, or R3 and R4 may be linked to each other to form a ring, R5 is a hydrogen atom or a $C_1$-$C_4$ alkyl radical, and the R5 radicals are either identical or different from each other, R6 is a hydrogen atom or a $C_1$-$C_4$ alkyl radical, and the R6 radicals are either identical or different from each other, R7 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R7 radicals are either identical or different from each other and two R7s may be linked to each other to form a ring, R8 is a hydrogen atom, a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R8 radicals are either identical or different from each other and two R8s may be linked to each other to form a ring, and X is a monovalent anion selected from a $C_1$-$C_{20}$ alkoxy radical having at least one hydrogen atom unsubstituted or substituted by a halogen atom, carboxy, alkylsulfinato, and amido, and the X monovalent anions are either identical or different from each other and each X may be coordinated to only a metallic zinc atom or form a bridged structure between two metallic zinc atoms.

3. The bimetallic zinc complex of claim 1 having one of formulae 5 and 6:

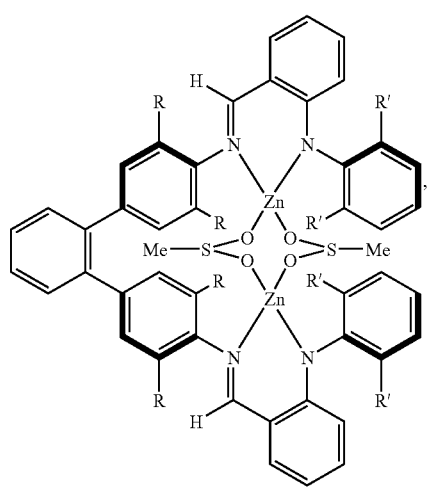

(5)

-continued

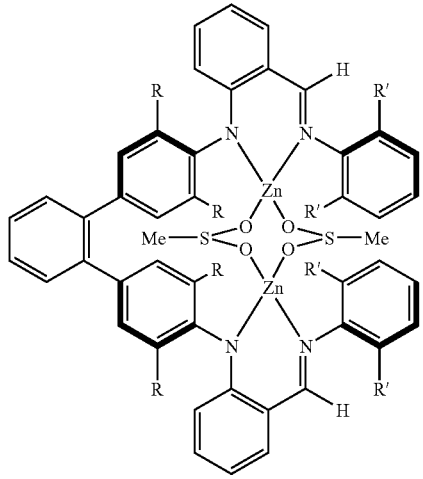

(6)

wherein each of R and R' is methyl, ethyl, or isopropyl, and

Me represents methyl.

4. A method of producing polycarbonate, comprising:

polymerizing an epoxy compound and carbon dioxide using the bimetallic zinc complex of claim 1 as a catalyst, the epoxy compound being selected from the group consisting of $C_2$-$C_{20}$ alkylene oxide unsubstituted or substituted by a halogen atom or alkoxy, $C_4$-$C_{20}$ cycloalkene oxide unsubstituted or substituted by a halogen atom or alkoxy, or $C_1$-$C_{10}$ styrene oxide unsubstituted or substituted by a halogen atom, alkoxy, or alkyl.

5. Polycarbonate produced using the method of claim 4.

6. The polycarbonate of claim 5, having a number average molecular weight of 5,000-1,000,000 and a molecular weight distribution of 1.05-4.0.

7. A compound having formula 3:

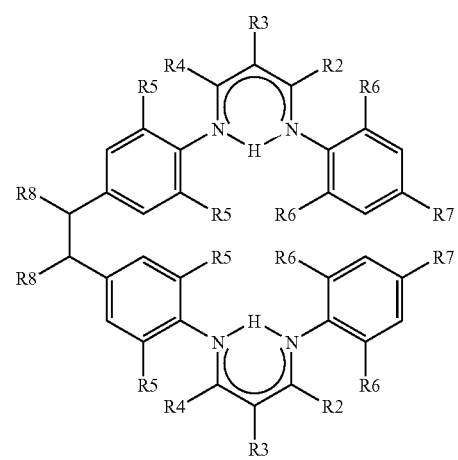

(3)

wherein

R2 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R2 radicals are either identical or different from each other, R3 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R3 radicals are either identical or different from each other, R4 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R4 radicals are either identical or different from each other, either R2 and R3, or R3 and R4 may be linked to each other to form a ring, R5 is a hydrogen atom or a $C_1$-$C_4$ alkyl radical, and the R5 radicals are either identical or different from each other, R6 is a hydrogen atom or a $C_1$-$C_4$ alkyl radical, and the R6 radicals are either identical or different from each other, R7 is a hydrogen atom, a halogen atom, a cyanide radical, or a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R7 radicals are either identical or different from each other and two R7s may be linked to each other to form a ring, R8 is a hydrogen atom, a $C_1$-$C_{20}$ alkyl radical having at least one hydrogen atom unsubstituted or substituted by a halogen atom, or a $C_6$-$C_{20}$ aryl radical having at least one hydrogen atom unsubstituted or substituted by a halogen atom, and the R8 radicals are either identical or different from each other and two R8s may be linked to each other to form a ring.

* * * * *